(12) United States Patent
Zoller et al.

(10) Patent No.: US 8,148,395 B2
(45) Date of Patent: Apr. 3, 2012

(54) AZOLOPYRIDIN-3-ONE DERIVATIVES AS INHIBITORS OF LIPASES AND PHOSPHOLIPASES

(75) Inventors: Gerhard Zoller, Frankfurt am Main (DE); Stefan Petry, Frankfurt am Main (DE); Gunter Muller, Frankfurt am Main (DE); Norbert Tennagels, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 327 days.

(21) Appl. No.: 12/235,047

(22) Filed: Sep. 22, 2008

(65) Prior Publication Data
US 2009/0054478 A1 Feb. 26, 2009

Related U.S. Application Data

(63) Continuation of application No. PCT/EP2007/002649, filed on Mar. 26, 2007.

(30) Foreign Application Priority Data
Mar. 28, 2006 (DE) .......................... 10 2006 014 688

(51) Int. Cl.
*A61K 31/44* (2006.01)
*C07D 471/02* (2006.01)
*C07D 491/02* (2006.01)
*C07D 498/02* (2006.01)

(52) U.S. Cl. ........................................ 514/300; 546/113
(58) Field of Classification Search .................. 546/113; 514/300
See application file for complete search history.

(56) References Cited

FOREIGN PATENT DOCUMENTS

| WO | WO 2004/037814 | 5/2004 |
| WO | 2004093872 | * 11/2004 |
| WO | WO 2004/093872 | 11/2004 |
| WO | WO 2004/094393 | 11/2004 |
| WO | WO 2005/073199 | 8/2005 |

* cited by examiner

*Primary Examiner* — Janet Andres
*Assistant Examiner* — Niloofar Rahmani
(74) *Attorney, Agent, or Firm* — Scully, Scott, Murphy & Presser, P.C.

(57) ABSTRACT

The present invention relates to azolopyridin-3-one derivatives of the general formula I with the meanings indicated in the description, their pharmaceutically usable salts and their use as medicinal substances.

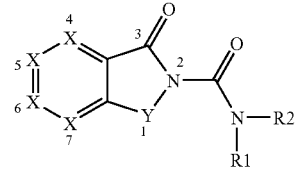

14 Claims, No Drawings

AZOLOPYRIDIN-3-ONE DERIVATIVES AS INHIBITORS OF LIPASES AND PHOSPHOLIPASES

This application is a Continuation of International Application No. PCT/EP2007/002649, filed Mar. 26, 2007, which is incorporated herein by reference in its entirety.

FIELD OF THE INVENTION

The present invention relates to azolopyridin-3-one derivatives of the general formula I, to their pharmaceutically useful salts and to their use as medicinal substances.

BACKGROUND OF THE INVENTION

Indazole compounds of similar structure are known from WO 2004/093872. Benzisoxazole compounds of similar structure are known from WO 2004/094393.

It is an object of the present invention to provide alternative compounds which have an inhibitory effect on endothelial lipase.

SUMMARY OF THE INVENTION

The invention relates to azolopyridin-3-one derivatives of the general formula I

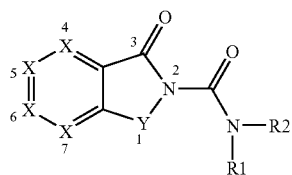

in which the meanings are:

X identically or differently =C(—R)— or =N—, where at least one and at most two X are =N—;
Y NR6 or O;
R identically or differently hydrogen, halogen, ($C_1$-$C_6$)-alkyl ($C_1$-$C_3$)-haloalkyl, ($C_1$-$C_3$)-alkyloxy-($C_1$-$C_3$)-alkylene, aryl, heterocycle, hydroxy, ($C_1$-$C_6$)-alkyloxy, ($C_1$-$C_3$)-haloalkyloxy, aryloxy, cyano, nitro, —S(O)$_p$—($C_1$-$C_6$)-alkyl, where p=0, 1 or 2, aminosulfonyl, pentafluorosulfanyl, amino, ($C_1$-$C_6$)-alkylamino, di-($C_2$-$C_{12}$)-alkylamino, —CO—($C_1$-$C_6$)-alkyl, —COOR3, —CO—NR4R5, —O—CO—NR4R5, —O—CO—($C_1$-$C_6$)-alkylene-CO—O—($C_1$-$C_6$)-alkyl, —O—CO—($C_1$-$C_6$)-alkylene-CO—O H or —O—CO—($C_1$-$C_6$)-alkylene-CO—NR4R5;
R1 ($C_5$-$C_{16}$)-alkyl, ($C_1$-$C_4$)-alkylene-aryl, ($C_1$-$C_4$)-alkylene-heterocycle, ($C_1$-$C_4$)-alkylene)-($C_3$-$C_{12}$)-cycloalkyl, ($C_8$-$C_{14}$)-bicycle, where aryl, heterocycle, cycloalkyl or bicycle may be substituted one or more times by preferably halogen, ($C_1$-$C_6$)-alkyl, ($C_1$-$C_3$)-alkyloxy, hydroxy, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylaminocarbonyl, ($C_1$-$C_6$)-alkoxycarbonyl, ($C_1$-$C_6$)-alkylcarbonyl, cyano, nitro, trifluoromethyl, trifluoromethyloxy, pentafluorosulfanyl, ($C_1$-$C_6$)-alkylsulfonyl, aminosulfonyl;
R2 hydrogen;
R3 hydrogen, ($C_1$-$C_6$)-alkyl, benzyl;
R4, R5 identically or differently hydrogen, ($C_1$-$C_6$)-alkyl, aryl, ($C_3$-$C_{12}$)-cycloalkyl, ($C_1$-$C_4$)-alkylene-aryl, ($C_1$-$C_4$)-alkylene-($C_3$-$C_{12}$)-cycloalkyl;
R6 hydrogen, ($C_1$-$C_{10}$)-alkyl, ($C_1$-$C_4$)-alkylene-CN, ($C_1$-$C_4$)-alkylene-aryl, ($C_1$-$C_4$)-alkylene-heterocycle, ($C_1$-$C_4$)-alkylene-($C_3$-$C_{12}$)-cycloalkyl, ($C_8$-$C_{14}$)-bicycle, where aryl, heterocycle, cycloalkyl or bicycle may be substituted one or more times by preferably halogen, ($C_1$-$C_6$)-alkyl, ($C_1$-$C_6$)-alkyloxy, hydroxy, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylaminocarbonyl, ($C_1$-$C_6$)-alkoxycarbonyl, ($C_1$-$C_6$)-alkylcarbonyl, cyano, trifluoromethyl, trifluoromethyloxy, nitro ($C_1$-$C_6$)-alkylsulfonyl, aminosulfonyl;
the tautomeric forms of the compounds and the physiologically tolerated salts thereof.

DETAILED DESCRIPTION OF THE INVENTION

Preferred compounds of the formula I are those in which
X is identically or differently =C(—R)— or =N—, where one X is =N—.

Preferred compounds of the formula I are also those in which
X is identically or differently =C(—R)— or =N—, where one X is =N—;
Y is NR6 or O;
R is identically or differently hydrogen, halogen, ($C_1$-$C_6$)-alkyl, hydroxy, phenoxy, trifluoromethyl, COOR3, pentafluorosulfanyl, amino, ($C_1$-$C_6$)-alkylamino, di-($C_2$-$C_{12}$)-alkylamino, ($C_1$-$C_6$)-alkylsulfonyl, aminosulfonyl, phenyl, ($C_5$-$C_7$)-heterocycle, ($C_1$-$C_6$)-alkylcarbonyl, CO—NR4R5, O—CO—NR4R5, O—CO—($C_1$-$C_6$)-alkylene-CO—O—($C_1$-$C_6$)-alkyl, O—CO—($C_1$-$C_6$)-alkylene-CO—NR4R5 or unsubstituted or mono- or poly-F-substituted ($C_1$-$C_3$)-alkyloxy;
R1 is ($C_6$-$C_{12}$)-alkyl, ($C_1$-$C_3$)-alkylene-aryl, ($C_1$-$C_3$)-alkylene-heterocycle, ($C_1$-$C_3$)-alkylene-($C_4$-$C_{12}$)-cycloalkyl, ($C_8$-$C_{14}$)-bicycle, where aryl, heterocycle, cycloalkyl or bicycle may be substituted one or more times by preferably halogen, ($C_1$-$C_6$)-alkyl, ($C_1$-$C_3$)-alkyloxy, hydroxy, amino, ($C_1$-$C_6$)-alkylamino, ($C_1$-$C_6$)-alkoxycarbonyl, ($C_1$-$C_6$)-alkylcarbonyl, cyano, trifluoromethyl, trifluoromethyloxy;
R2 is hydrogen;
R3 is hydrogen, ($C_1$-$C_6$)-alkyl, benzyl;
R4, R5 are identically or differently hydrogen, ($C_1$-$C_6$)-alkyl, ($C_3$-$C_{12}$)-cycloalkyl, phenyl, ($C_1$-$C_4$)-alkylene-phenyl, ($C_1$-$C_4$)-alkylene-($C_4$-$C_{12}$)-cycloalkyl;
R6 is hydrogen, ($C_1$-$C_{10}$)-alkyl, ($C_1$-$C_4$)-alkylene-CN, ($C_1$-$C_4$)-alkylene-phenyl, ($C_1$-$C_4$)-alkylene-heterocycle, ($C_1$-$C_4$)-alkylene-($C_3$-$C_{12}$)-cycloalkyl, where phenyl, heterocycle, cycloalkyl may be substituted one or more times by preferably halogen, ($C_1$-$C_6$)-alkyl, ($C_1$-$C_3$)-alkyloxy, hydroxy, ($C_1$-$C_6$)-alkoxycarbonyl, ($C_1$-$C_6$)-alkylcarbonyl, cyano, trifluoromethyl, trifluoromethyloxy, ($C_1$-$C_6$)-alkylsulfonyl;
the tautomeric forms of the compounds and the physiologically tolerated salts thereof.

Preferred compounds of the formula I are also those in which
X in position 5 and 6 is identically or differently =C(—R)—, in position 7 or 4 is =N—.

Further preferred compounds are those of the formula I in which
X in position 4, 5 and 6 is identically or differently =C(—R)—, in position 7 is =N—.

Particularly preferred compounds of the formula I are those in which the meanings are X identically or differently =C(—R)— or =N—, where one X is =N—;
Y NR6 or O;
R identically or differently hydrogen, halogen, $(C_1-C_6)$-alkyl, trifluoro-methyl, hydroxy, amino, $(C_1-C_6)$-alkylcarbonyl, COOR3, $(C_1-C_6)$-alkylsulfonyl, pentafluorosulfanyl, or unsubstituted or mono- or poly-F-substituted $(C_1-C_3)$-alkyloxy;
R1 $(C_6-C_{10})$-alkyl, —CH$_2$-phenyl, $(C_1-C_2)$-alkylene-heteroaryl or bicycle of the formula Ic

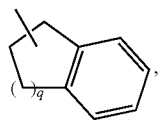
Ic with q=1 or 2,
where phenyl, heteroaryl or bicycle of the formula Ic may be substituted once to twice by preferably halogen, $(C_1-C_6)$-alkyl, $(C_1-C_6)$-alkyloxy, hydroxy, amino, $(C_1-C_6)$-alkoxycarbonyl, $(C_1-C_6)$-alkylcarbonyl, cyano, trifluoromethyl, trifluoromethyloxy;
R2 hydrogen;
R3 hydrogen, $(C_1-C_6)$-alkyl;
R6 hydrogen $(C_1-C_8)$-alkyl, $(C_1-C_2)$-alkylene-CN, $(C_1-C_4)$-alkylene-phenyl, $(C_1-C_4)$-alkylene-$(C_4-C_{12})$-heteroaryl, where phenyl or heteroaryl may be substituted one or more times by halogen, $(C_1-C_6)$-alkyl, $(C_1-C_3)$-alkyloxy, hydroxy, $(C_1-C_6)$-alkoxycarbonyl, $(C_1-C_6)$-alkylcarbonyl, trifluoromethyl;
the tautomeric forms of the compounds and the physiologically tolerated salts thereof.

In a particularly preferred embodiment of the compounds of the formula I
Y is NR6.

In another particularly preferred embodiment of the compounds of the formula I
Y is O.

Very particularly preferred compounds of the formula I are those in which
X is identically or differently =C(—R)— or =N—, where one X is =N—;
Y is NR6 or O;
R is identically or differently hydrogen, halogen, hydroxy, $(C_1-C_6)$-alkyloxy, trifluoromethyl $(C_1-C_6)$-alkylcarbonyl or $(C_1-C_6)$-alkyl;
R1 is $(C_6-C_{10})$-alkyl, —CH$_2$-phenyl, $(C_1-C_3)$-alkylene-thienyl or bicycle of the formula Ic

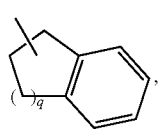
Ic with q=1 or 2, where phenyl, thienyl or bicycle may be substituted once to twice by halogen, $(C_1-C_6)$-alkyl, $(C_1-C_3)$-alkyloxy, $(C_1-C_6)$-alkylcarbonyl, trifluoromethyl;
R2 is hydrogen;
R6 is hydrogen, $(C_1-C_6)$-alkyl, $(C_1-C_2)$-alkylene-CN, $(C_1-C_2)$-alkylene-phenyl, where phenyl may be substituted one or more times by halogen, $(C_1-C_6)$-alkyl, $(C_1-C_3)$-alkyloxy, hydroxy, $(C_1-C_6)$-alkylcarbonyl, trifluoromethyl;
the tautomeric forms of the compounds and the physiologically tolerated salts thereof.

More very particularly preferred compounds of the formula I are those in which the meanings are
X identically or differently =C(—R)— or =N—, where one X is =N—;
Y NR6 or O;
R identically or differently hydrogen, F, Cl, hydroxy, $(C_1-C_6)$-alkyloxy, trifluoromethyl $(C_1-C_6)$-alkylcarbonyl or $(C_1-C_6)$-alkyl;
R1 $(C_6-C_{10})$-alkyl, —CH$_2$-phenyl, $(C_1-C_2)$-alkylene-thienyl or bicycle of the formula Ic

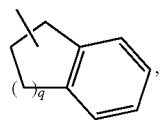
Ic with q=1 or 2, where phenyl, thienyl or bicycle may be substituted one to twice by F, Cl, $(C_1-C_6)$-alkyl, $(C_1-C_3)$-alkyloxy, $(C_1-C_6)$-alkylcarbonyl, trifluoromethyl;
R2 hydrogen;
R6 hydrogen, $(C_1-C_6)$-alkyl, $(C_1-C_2)$-alkylene-CN, $(C_1-C_2)$-alkylene-phenyl, where phenyl may be substituted one or more times by halogen, $(C_1-C_6)$-alkyl, $(C_1-C_3)$-alkyloxy, hydroxy, $(C_1-C_6)$-alkylcarbonyl, trifluoromethyl;
the tautomeric forms of the compound and the physiologically tolerated salts thereof.

A particular particularly preferred compounds of the formula I are those in which the meanings are
X identically or differently =C(—R)— or =N—, where one X is =N—;
Y NR6 or O;
R identically or differently hydrogen, Cl, hydroxy, methyl, trifluoromethyl;
R1 $(C_6-C_{10})$-alkyl, —CH$_2$-phenyl, $(C_1-C_2)$-alkylene-thienyl or bicycle of the formula Id

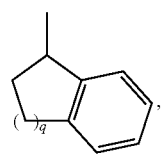
Id with q=1 or 2, where phenyl may be substituted by, methyl or ethyl;
R2 hydrogen;
R6 hydrogen, CH$_2$—CN, methyl, butyl, benzyl;
the tautomeric forms of the compound and the physiologically tolerated salts thereof.

The invention relates to compounds of the formula I in the form of their salts, racemates, racemic mixtures and pure enantiomers, and to their diastereomers and mixtures thereof.

The alkyl and alkylene radicals in the substituents R, R1, R2, R3, R4, R5 and R6 may be either straight-chain or branched. Halogen is fluorine, chlorine, bromine or iodine, in particular fluorine or chlorine.

Haloalkyl is an alkyl which is substituted once, more than once or completely by halogen.

Preferred halogens are fluorine and chlorine.

A cycloalkyl radical means a ring system which comprises one or more rings, which is saturated or partially unsaturated (having one or two double bonds) and which is composed exclusively of carbon atoms, such as, for example cyclopropyl, cyclopentyl, cyclopentenyl, cyclohexyl or adamantyl. The cycloalkyl radicals may be substituted one or more times by suitable groups such as, for example: F, Cl, Br, I, $CF_3$, $NO_2$, $N_3$, CN, COOH, $COO(C_1-C_6)$alkyl, $CONH_2$, $CONH(C_1-C_6)$alkyl, $CON[(C_1-C_6)alkyl]_2$, cycloalkyl, $(C_1-C_{10})$-alkyl, $(C_2-C_6)$-alkenyl, $(C_2-C_6)$-alkynyl, $O-(C_1-C_6)$-alkyl $O-CO-(C_1-C_6)$-alkyl, $O-CO-(C_1-C_6)$-aryl, $O-CO-(C_1-C_6)$-heterocycle; $PO_3H_2$, $SO_3H$, $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-aryl, $S-(CH_2)_n$-heterocycle, $SO-(C_1-C_6)$-alkyl, $SO-(CH_2)_n$-aryl, $SO-(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N(C_1-C_6)$-alkyl$)(CH_2)_n$-aryl, $SO_2-N(C_1-C_6)$-alkyl$)(CH_2)_n$-heterocycle, $SO_2-N((CH_2)_n$-aryl$)_2$, $SO_2-N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, $O-(C_1-C_6)$-alkyl, $(C_1-C_6)$-alkyl, $NH_2$; $C(NH)(NH_2)$, $NH_2$, $NH-(C_1-C_6)$-alkyl, $N((C_1-C_6)$-alkyl$)_2$, $NH(C_1-C_7)$-acyl, $NH-CO-(C_1-C_6)$-alkyl, $NH-COO-(C_1-C_6)$-alkyl, $NH-CO$-aryl, $NH-CO$-heterocycle, $NH-COO$-aryl, $NH-COO$-heterocycle, $NH-CO-NH-(C_1-C_6)$-alkyl, $NH-CO-NH$-aryl, $NH-CO-NH$-heterocycle, $N(C_1-C_6)$-alkyl-$CO-(C_1-C_6)$-alkyl, $N(C_1-C_6)$-alkyl -$COO-(C_1-C_6)$-alkyl, $N(C_1-C_6)$-alkyl-$CO$-aryl, $N(C_1-C_6)$-alkyl-$CO$-heterocycle, $N(C_1-C_6)$-alkyl-$COO$-aryl, $N(C_1-C_6)$-alkyl-$COO$-heterocycle, $N(C_1-C_6)$-alkyl-$CO-NH-(C_1-C_6)$-alkyl), $N(C_1-C_6)$-alkyl-$CO-NH$-aryl, $N(C_1-C_6)$-alkyl-$CO-NH$-heterocycle, $N((C_1-C_6)$-alkyl$)$-$CO-N-(C_1-C_6)$-alkyl$)_2$, $N((C_1-C_6)$-alkyl$)$-$CO-N((C_1-C_6)$-alkyl$)$-aryl, $N((C_1-C_6)$-alkyl$)$-$CO-N((C_1-C_6)$-alkyl$)$-heterocycle, $N((C_1-C_6)$-alkyl$)$-$CO-N$-(aryl)$_2$, $N((C_1-C_6)$-alkyl$)$-$CO-N$-(heterocycle)$_2$, $N(aryl)$-$CO-(C_1-C_6)$-alkyl, $N(heterocycle)$-$CO-(C_1-C_6)$-alkyl, $N(aryl)$-$COO-(C_1-C_6)$-alkyl, $N(heterocycle)$-$COO-(C_1-C_6)$-alkyl, $N(Aryl)$-$CO$-aryl, $N(heterocycle)$-$CO$-aryl, $N(aryl)$-$COO$-aryl, $N(heterocycle)$-$COO$-aryl, $N(aryl)$-$CO-NH-(C_1-C_6)$-alkyl), $N(heterocycle)$-$CO-NH-(C_1-C_6)$-alkyl), $N(aryl)$ -$CO-NH$-aryl, $N(heterocycle)$-$CO-NH$-aryl, $N(aryl)$-$CO-N-(C_1-C_6)$-alkyl$)_2$, $N(heterocycle)$-$CO-N-(C_1-C_6)$-alkyl$)_2$, $N(aryl)$-$CO-N((C_1-C_6)$-alkyl$)$-aryl, $N(heterocycle)$-$CO-N((C_1-C_6)$-alkyl$)$-aryl, $N(aryl)$-$CO-N$-(aryl)$_2$, $N(heterocycle)$-$CO-N$-(aryl)$_2$, aryl, $O-(CH_2)_n$-aryl, $O-(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl, $CONH_2$.

Bicycle is a partly unsaturated bicyclic ring system having 8 to 14 ring members which has exclusively carbon atoms as ring members. This definition includes ring systems which comprise a fused benzene nucleus. Examples which may be mentioned are the tetrahydronaphthyl, alpha- or beta-tetralone, indanyl or indan-1-on-yl radical. Preferred bicycle radicals are the tetrahydronaphthyl and indanyl. The bicyclic radicals may be substituted one or more times by suitable groups such as, for example: F, Cl, Br, I, $CF_3$, $NO_2$, $N_3$, CN, COOH, $COO(C_1-C_6)$alkyl, $CONH_2$, $CONH(C_1-C_6)$alkyl, $CON[(C_1-C_6)alkyl]_2$, cycloalkyl, $(C_1-C_{10})$-alkyl, $(C_2-C_6)$-alkenyl, $(C_2-C_6)$-alkynyl, $O-(C_1-C_6)$-alkyl $O-CO-(C_1-C_6)$-alkyl, $O-CO-(C_1-C_6)$-aryl, $O-CO-(C_1-C_6)$-heterocycle; $PO_3H_2$, $SO_3H$, $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-aryl, $S-(CH_2)_n$-heterocycle, $SO-(C_1-C_6)$-alkyl, $SO-(CH_2)_n$-aryl, $SO-(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N(C_1-C_6)$-alkyl$)(CH_2)_n$-aryl, $SO_2-N(C_1-C_6)$-alkyl$)(CH_2)_n$-heterocycle, $SO_2-N((CH_2)_n$-aryl$)_2$, $SO_2-N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, $O-(C_1-C_6)$-alkyl, $(C_1-C_6)$-alkyl, $NH_2$; $C(NH)(NH_2)$, $NH_2$, $NH-(C_1-C_6)$-alkyl, $N((C_1-C_6)$-alkyl$)_2$, $NH(C_1-C_7)$-acyl, $NH-CO-(C_1-C_6)$-alkyl, $NH-COO-(C_1-C_6)$-alkyl, $NH-CO$-aryl, $NH-CO$-heterocycle, $NH-COO$-aryl, $NH-COO$-heterocycle, $NH-CO-NH-(C_1-C_6)$-alkyl, $NH-CO-NH$-aryl, $NH-CO-NH$-heterocycle, $N(C_1-C_6)$-alkyl $-CO-(C_1-C_6)$-alkyl, $N(C_1-C_6)$-

An aryl radical means a phenyl or a naphthyl radical. The aryl radicals may be substituted one or more times by suitable groups such as, for example: F, Cl, Br, I, $CF_3$, $NO_2$, CN, COOH, $COO(C_1-C_6)$alkyl, $CONH_2$, $CONH(C_1-C_6)$alkyl, $CON[(C_1-C_6)alkyl]_2$ $(C_3-C_{10})$-cycloalkyl, $(C_1-C_{10})$-alkyl, $(C_2-C_6)$-alkenyl, $(C_2-C_6)$-alkynyl, $O-(C_1-C_6)$-alkyl $O-CO-(C_1-C_6)$-alkyl, $O-CO-(C_1-C_6)$-aryl, $PO_3H_2$, $SO_3H$, $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-aryl, $S-(CH_2)_n$-heterocycle, $SO-(C_1-C_6)$-alkyl, $SO-(CH_2)_n$-aryl, $SO-(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N(C_1-C_6)$-alkyl$)(CH_2)_n$-aryl, $SO_2-N(C_1-C_6)$-alkyl$)(CH_2)_n$-heterocycle, $SO_2-N((CH_2)_n$-aryl$)_2$, $SO_2-N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, $O-(C_1-C_6)$-alkyl, $(C_1-C_6)$-alkyl, $NH_2$; $C(NH)(NH_2)$, $NH_2$, $NH-(C_1-C_6)$-alkyl, $N((C_1-C_6)$-alkyl$)_2$, $NH(C_1-C_7)$-acyl, $NH-CO-(C_1-C_6)$-alkyl, $NH-COO-(C_1-C_6)$-alkyl, $NH-CO$-aryl, $NH-CO$-heterocycle, $NH-COO$-aryl, $NH-COO$-heterocycle, $NH-CO-NH-(C_1-C_6)$-alkyl, $NH-CO-NH$-aryl, $NH-CO-NH$-heterocycle, $N(C_1-C_6)$-alkyl $-CO-(C_1-C_6)$-alkyl, $N(C_1-C_6)$- alkyl —COO—$(C_1$-$C_6)$-alkyl, $N(C_1$-$C_6)$ -alkyl-CO-aryl, $N(C_1$-$C_6)$-alkyl-CO-heterocycle, $N(C_1$-$C_6)$-alkyl-COO-aryl, $N(C_1$-$C_6)$-alkyl-COO-heterocycle, $N(C_1$-$C_6)$-alkyl-CO—NH—$(C_1$-$C_6)$-alkyl), $N(C_1$-$C_6)$-alkyl-CO—NH-aryl, $N(C_1$-$C_6)$-alkyl-CO—NH-heterocycle, $N((C_1$-$C_6)$-alkyl)-CO—N—$(C_1$-$C_6)$-alkyl)$_2$, $N((C_1$-$C_6)$-alkyl)-CO—N$((C_1$-$C_6)$-alkyl)-aryl, $N((C_1$-$C_6)$-alkyl)-CO—N$((C_1$-$C_6)$-alkyl)-heterocycle, $N((C_1$-$C_6)$-alkyl)-CO—N-(aryl)$_2$, $N((C_1$-$C_6)$-alkyl)-CO—N-(heterocycle)$_2$, N(aryl)-CO—$(C_1$-$C_6)$-alkyl, N(heterocycle)-CO—$(C_1$-$C_6)$-alkyl, N(aryl)-COO—$(C_1$-$C_6)$-alkyl, N(heterocycle)-COO—$(C_1$-$C_6)$-alkyl, N(aryl)-CO-aryl, N(heterocycle)-CO-aryl, N(aryl)-COO-aryl, N(heterocycle)-COO-aryl, N(aryl)-CO—NH—$(C_1$-$C_6)$-alkyl), N(heterocycle)-CO—NH—$(C_1$-$C_6)$-alkyl), N(aryl)-CO—NH-aryl, N(heterocycle)-CO—NH-aryl, N(aryl)-CO—N—$(C_1$-$C_6)$-alkyl)$_2$, N(heterocycle)-CO—N—$(C_1$-$C_6)$-alkyl)$_2$, N(aryl)-CO—N$((C_1$-$C_6)$-alkyl)-Aryl, N(heterocycle)-CO—N$((C_1$-$C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1$-$C_6)$-alkyl, $(C_1$-$C_6)$-alkyl, $NH_2$, $NH(C_1$-$C_6)$-alkyl, $N((C_1$-$C_6)$-alkyl)$_2$, $SO_2$—$CH_3$, COOH, COO—$(C_1$-$C_6)$-alkyl, $CONH_2$.

Heterocycle is a mono- or bicyclic ring system having 5 to 12 ring members, in which at least one atom of the ring system is a heteroatom from the series N, O and S. This definition also includes ring systems in which the heterocycle is fused to a benzene nucleus. $(C_5$-$C_7)$-Heterocycle is a monocyclic, $(C_8$-$C_{12})$-heterocycle is a bicyclic ring system.

Suitable "heterocyclic rings" or "heterocyclic radicals" are azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxa-diazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadiazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of these compounds, thus for example 1-oxy-2-, 3- or 4-pyridyl.

The heterocyclic rings or heterocyclic radicals may be substituted one or more times by suitable groups such as, for example: F, Cl, Br, I, $CF_3$, $NO_2$, $N_3$, CN, COOH, COO($C_1$-$C_6$)alkyl, $CONH_2$, $CONH(C_1$-$C_6)$alkyl, $CON[(C_1$-$C_6)$ alkyl]$_2$, $(C_1$-$C_6)$-alkyl, $(C_2$-$C_6)$-alkenyl, $(C_2$-$C_6)$-alkynyl, O—$(C_1$-$C_6)$-alkyl, where one, more than one or all hydrogen(s) in the alkyl radicals may be replaced by fluorine; $PO_3H_2$, $SO_3H$, $SO_2$—$NH_2$, $SO_2NH(C_1$-$C_6)$ -alkyl, $SO_2N[(C_1$-$C_6)$-alkyl]$_2$, S—$(C_1$-$C_6)$-alkyl, S—$(CH_2)_n$-phenyl, SO—$(C_1$-$C_6)$-alkyl, SO—$(CH_2)_n$-phenyl, $SO_2$—$(C_1$-$C_6)$-alkyl, $SO_2$—$(CH_2)_n$-phenyl, where n may be 0-6, and the phenyl radical may be substituted up to twice by F, Cl, Br, OH, $CF_3$, $NO_2$, CN, $OCF_3$, O—$(C_1$-$C_6)$-alkyl, $(C_1$-$C_6)$-alkyl, $NH_2$; $C(NH)(NH_2)$, $NH_2$, NH—$(C_1$-$C_6)$-alkyl, $N((C_1$-$C_6)$-alkyl)$_2$, $NH(C_1$-$C_7)$-acyl, phenyl, O—$(CH_2)_n$-phenyl, where n may be 0-6, where the phenyl ring may be substituted one to 3 times by F, Cl, Br, I, OH, $CF_3$, $NO_2$, CN, $OCF_3$, O—$(C_1$-$C_6)$-alkyl, $(C_1$-$C_6)$-alkyl, $NH_2$, $NH(C_1$-$C_6)$-alkyl, $N((C_1$-$C_6)$-alkyl)$_2$, $SO_2$—$CH_3$, COOH, COO—$(C_1$-$C_6)$-alkyl, $CONH_2$.

Heteroaryl is a mono- or bicyclic aromatic ring system having 5 to 12 ring members, in which at least one atom of the ring system is a heteroatom from the series N, O and S. This definition also includes ring systems in which the heteroaryl is fused with a benzene nucleus. Examples of suitable "heteroaryl rings" or "heteroaryl radicals" are benzimidazolyl, benzofuranyl, benzothiophenyl, benzoxazolyl, benzthiazolyl, benztriazolyl, benztetrazolyl, benzisoxazolyl, benzisothiazolyl, quinolinyl, furyl, furazanyl, imidazolyl, 1H-indazolyl, indolyl, 1,2,3-oxadiazolyl, 1,2,4-oxadiazolyl, 1,2,5-oxadiazolyl, 1,3,4-oxadiazolyl, pyrimidinyl, pyrazinyl, pyrazolyl, pyridyl, pyrrolyl, thiazolyl, 1,2,3-thiadiazolyl, 1,2,4-thiadiazolyl, 1,2,5-thiadiazolyl, 1,3,4-thiadiazolyl, thiophenyl. The heteroaryl rings or heteroaryl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, $CONH(C_1$-$C_6)$alkyl, $CON[(C_1$-$C_6)$ alkyl]$_2$, $(C_1$-$C_6)$-alkyl, $(C_2$-$C_6)$-alkenyl, $(C_2$-$C_6)$-alkynyl, O—$(C_1$-$C_6)$-alkyl, where one, more than one or all hydrogen(s) in the alkyl radicals may be replaced by fluorine; $PO_3H_2$, $SO_3H$, $SO_2$—$NH_2$, $SO_2NH(C_1$-$C_6)$-alkyl, $SO_2N[(C_1$-$C_6)$ -alkyl]$_2$, S—$(C_1$-$C_6)$-alkyl, S—$(CH_2)_n$-phenyl, SO—$(C_1$-$C_6)$-alkyl, SO—$(CH_2)_n$-phenyl, $SO_2$—$(C_1$-$C_6)$-alkyl, $SO_2$—$(CH_2)_n$-phenyl, where n may be 0-6, and the phenyl radical may be substituted up to twice by F, Cl, Br, OH, $CF_3$, $NO_2$, CN, $OCF_3$, O—$(C_1$-$C_6)$-alkyl, $(C_1$-$C_6)$ -alkyl, $NH_2$; $C(NH)(NH_2)$, $NH_2$, NH—$(C_1$-$C_6)$-alkyl, $N((C_1$-$C_6)$-alkyl)$_2$, $NH(C_1$-$C_7)$-acyl, phenyl, O—$(CH_2)_n$-phenyl, where n may be 0-6, where the phenyl ring may be substituted one to 3 times by F, Cl, Br, I, OH, $CF_3$, $NO_2$, CN, $OCF_3$, O—$(C_1$-$C_6)$-alkyl, $(C_1$-$C_6)$ -alkyl, $NH_2$, $NH(C_1$-$C_6)$-alkyl, $N((C_1$-$C_6)$-alkyl)$_2$, $SO_2$—$CH_3$, COOH, COO—$(C_1$-$C_6)$-alkyl, $CONH_2$.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the invention of the formula I, for example an ester, which on administration to a mammal such as, for example, a human is able to form (directly or indirectly) a compound of the formula I or an active metabolite thereof.

Physiologically functional derivatives also include prodrugs of the compounds of the invention as, for example, described in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

The compounds of the invention of the general formula I have a surprising inhibitory effect on endothelial lipase (EL). The preferred substrate for EL is HDL, which has antiatherosclerotic activity. A reduction in the HDL level leads to progression of atherosclerosis and its sequelae such as coronary heart diseases and in addition promotes the development of metabolic syndrome and its sequela diabetes. An inhibition of EL should thus generally lead to prevention of atherosclerotic disorders and in people with an increased risk of diabetes, indirectly reduce the probability of the disorder.

It has further been found that the inhibitory effect of the compounds of the invention of the general formula I is selective in relation to other lipases.

The compounds of the formula I are notable for exhibiting an improved solubility compared with compounds of similar structure in aqueous media with at least the same time high activity. Preferred compounds of the invention further exhibit an improved metabolic stability compared with compounds of the prior art. Furthermore the compounds of the invention show advantages in terms of serum stability.

Compounds of this type are particularly suitable for the treatment and/or prevention of 1. Dyslipidemias and the sequelae thereof such as, for example, atherosclerosis, coronary heart disease, cerebrovascular disorders etc., especially those (but not restricted thereto) which are characterized by one or more of the following factors:
   high plasma triglyceride concentrations, high postprandial plasma triglyceride concentrations
   low HDL cholesterol concentration
   low apoA lipoprotein concentrations
   high LDL cholesterol concentrations
   small dense LDL cholesterol particles
   high apoB lipoprotein concentrations
2. Various other conditions which may be associated with the metabolic syndrome, such as:
   obesity (excess weight), including central obesity
   thromboses, hypercoagulable and prothrombotic stages (arterial and venous)
   high blood pressure
   heart failure such as, for example (but not restricted thereto), following myocardial infarction, hypertensive heart disease or cardiomyopathy
   diabetes mellitus, in particular type 2 diabetes including the prevention of the sequelae associated therewith (hyperglycemia, glucose intolerance, loss of β-cells of the pancreas, macro- and microvascular disorders)
3. Other disorders or conditions in which inflammatory reactions or cell differentiation may for example be involved are:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   pancreatitis
   other inflammatory states
   retinopathy
   adipose cell tumors
   adipose cell carcinomas such as, for example, liposarcoma
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and of the urinary tract, of the genital tract, prostate carcinomas etc.
   acute and chronic myeloproliferative disorders and lymphomas
   angiogenesis
   neurodegenerative disorders
   Alzheimer's disease
   multiple sclerosis
   Parkinson's disease
   erythemato-squamous dermatoses such as, for example, psoriasis
   acne vulgaris
   other skin disorders and dermatological conditions which are modulated by PPAR
   eczemas and neurodermatitis
   dermatitis such as, for example, seborrheic dermatitis or photodermatitis
   keratitis and keratosis such as, for example, seborrheic keratoses, senile keratoses, actinic keratosis, photo-induced keratoses or keratosis follicularis
   keloids and keloid prophylaxis
   warts, including condylomata or condylomata acuminata
   human papilloma viral (HPV) infections, such as, for example, venereal papillomata, viral warts such as, for example, molluscum contagiosum, leukoplakia
   papular dermatoses such as, for example, lichen planus
   skin cancer such as, for example, basal cell carcinoma, melanomas or cutaneous T-cell lymphomas
   localized benign epidermal tumors such as, for example, keratoderma, epidermal naevi
   chilblains
   high blood pressure
   syndrome X
   polycystic ovary syndrome (PCOS)
   asthma
   osteoarthritis
   lupus erythematosus (LE) or inflammatory rheumatic disorders such as, for example, rheumatoid arthritis
   vasculitis
   wasting (cachexia)
   gout
   ischemia/reperfusion syndrome
   acute respiratory distress syndrome (ARDS)

Formulations

The amount of a compound of the invention necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of the invention. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on lipid metabolism disorders. They beneficially influence the ratio of HDL to LDL and particularly increase the HDL level and are suitable for the prevention and treatment of dyslipidemias and metabolic syndrome and the diverse sequelae thereof such as atherosclerosis, coronary heart disease, heart failure, obesity and diabetes.

Combinations with Other Medicaments

The compounds of the invention can be administered alone or in combination with one or more further pharmacologically active ingredients. In particular, the compounds of the invention can be administered with active ingredients which have a similar pharmacological effect to themselves. For example, they can be administered in combination with active ingredients which have favorable effects on metabolic disturbances or disorders frequently associated therewith. Examples of such medicaments are 1. medicaments which lower blood glucose, antidiabetics,
    2. active ingredients for the treatment of dyslipidemias,
    3. antiatherosclerotic medicaments,
    4. antiobesity agents,
    5. antiinflammatory active ingredients
    6. active ingredients for the treatment of malignant tumors
    7. antithrombotic active ingredients 8. active ingredients for the treatment of high blood pressure
9. active ingredients for the treatment of heart failure and
10. active ingredients for the treatment and/or prevention of complications caused by diabetes or associated with diabetes
11. active ingredients for the treatment of neurodegenerative diseases
12. active ingredients for the treatment of diseases of the central nervous system
13. active ingredients for the treatment of dependence on drugs, nicotine and alcohol
14. analgesics They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Further active ingredients particularly suitable for the combination products are: All antidiabetics which are mentioned in the Rote Liste 2006, chapter 12; all weight -reducing agents/appetite suppressants which are mentioned in the Rote Liste 2006, chapter 1; all lipid-lowering agents which are mentioned in the Rote Liste 2006, chapter 58. They can be combined with the compound of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation. Most of the active ingredients mentioned hereinafter are disclosed in the USP Dictionary of USAN and International Drug Names, US Pharmacopeia, Rockville 2001. Antidiabetics include insulin and insulin derivatives such as, for example, Lantus® (see www.lantus.com) or HMR 1964 or those described in WO 2005/005477 (Novo Nordisk), fast-acting insulins (see U.S. Pat. No. 6,221,633), inhalable insulins such as, for example, Exubera® or oral insulins such as, for example, IN-105 (Nobex) or Oral-lyn™ (Generex Biotechnology), GLP-1-derivatives such as, for example, exenatide, liraglutide or those which have been disclosed in WO 98/08871 or WO 2005/027978 of Novo Nordisk A/S, in WO 01/04156 of Zealand or in WO 00/34331 of Beaufourlpsen, Pramlintide Acetate (Symlin; Amylin Pharmaceuticals), and orally effective hypoglycemic active ingredients.

The active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine-fructose-6-phosphate amidotransferase (GFAT),
GLP-1 agonists,
potassium channel openers such as, for example, those which have been disclosed in WO 97/26265 and WO 99/03861 of Novo Nordisk A/S,
inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I is administered in combination with an HMGCoA reductase inhibitor such as simvastatin, fluvastatin, pravastatin, lovastatin, atorvastatin, cerivastatin, rosuvastatin or L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO 2005/042692), MD-0727 (Microbia Inc., WO 2005/021497) or with compounds as described in WO 2002/066464 (Kotobuki Pharmaceutical Co. Ltd.), WO 2005/062824 (Merck & Co.) or WO 2005/061451 and WO 2005/061452 (AstraZeneca AB).

In one embodiment of the invention, the compound of the formula I is administered in combination with a PPAR gamma agonist such as, for example, rosiglitazone, pioglitazone, JTT-501, G1262570, R-483 or CS-011 (rivoglitazone).

In one embodiment of the invention, the compound of the formula I is administered in combination with a PPAR alpha agonist such as, for example, GW9578, GW-590735, K-111, LY-674, KRP-101 or DRF-10945.

In one embodiment of the invention, the compound of the formula I is administered in combination with a mixed PPAR alpha/gamma agonist such as, for example, muraglitazar, tesaglitazar, naveglitazar, LY-510929, ONO-5129, E-3030 or as described in WO 00/64888, WO 00/64876, WO 03/020269, WO 2004/075891, WO 2004/076402, WO 2004/075815, WO 2004/076447, WO 2004/076428, WO 2004/076401, WO 2004/076426, WO 2004/076427, WO 2006/018118, WO 2006/018115, and WO 2006/018116 or in J. P. Berger et al., TRENDS in Pharmacological Sciences 28(5), 244-251, 2005.

In one embodiment of the invention, the compound of the formula I is administered in combination with a PPAR delta agonist such as, for example, GW-501516, or as described in WO 2005/097762, WO 2005/097786, WO2005/097763, WO 2006/029699.

In one embodiment of the invention, the compound of the formula I is administered in combination with metaglidasen or with MBX-2044 or other partial PPAR gamma agonists/antagonists.

In one embodiment of the invention, the compound of the formula I is administered in combination with a fibrate such as, for example, fenofibrate, clofibrate or bezafibrate.

In one embodiment of the invention, the compound of the formula I is administered in combination with an MTP inhibitor such as, for example, implitapide, BMS-201038, R-103757 or those described in WO 2005/085226.

In one embodiment of the invention, the compound of the formula I is administered in combination with a CETP inhibitor such as, for example, torcetrapib or JTT-705.

In one embodiment of the invention, the compound of the formula I is administered in combination with a bile acid absorption inhibitor (see, for example, U.S. Pat. No. 6,245,744, U.S. Pat. No. 6,221,897 or WO 00/61568), such as, for example, HMR 1741 or those as described in DE 10 2005 033099.1 and DE 10 2005 033100.9.

In one embodiment of the invention, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those as described in WO 2005/097738.

In one embodiment, the compound of the formula I is administered in combination with Omacor® (Omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494 or as described in WO 2005/077907.

In one embodiment of the invention, the compound of the formula I is administered in combination with a lipoprotein (a) antagonist such as, for example, gemcabene (CI-1027).

In one embodiment of the invention, the compound of the formula I is administered in combination with an HM74A receptor agonist such as, for example, nicotinic acid.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment of the invention, the compound of the formula I is administered in combination with a sulfonylurea such as, for example, tolbutamide, glibenclamide, glipizide or glimepiride.

In one embodiment of the invention, the compound of the formula I is administered in combination with a biguanide such as, for example, metformin.

In another embodiment of the invention, the compound of the formula I is administered in combination with a meglitinide such as, for example, repaglinide or nateglinide.

In one embodiment of the invention, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment of the invention, the compound of the formula I is administered in combination with an α-glucosidase inhibitor such as, for example, miglitol or acarbose.

In one embodiment of the invention, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of the formula I is administered in combination with an inhibitor of glycogen phosphorylase, such as, for example, PSN-357 or FR-258900 or those as described in WO 2003/084922, WO 2004/007455, WO 2005/073229-31 or WO 2005/067932.

In one embodiment of the invention, the compound of the formula I is administered in combination with glucagon receptor antagonists such as, for example, A-770077, NNC-25-2504 or as described in WO 2004/100875 or WO 2005/065680.

In one embodiment of the invention, the compound of the formula I is administered in combination with activators of glucokinase, such as, for example, RO-4389620, LY-2121260 (WO 2004/063179), PSN-105, PSN-110, GKA-50 or those as are described for example by Prosidion in WO 2004/072031, WO 2004/072066, WO 05/103021 or WO 06/016178, by Roche in WO 00/058293, WO 00/183465, WO 00/183478, WO 00/185706, WO 00/185707, WO 01/044216, GB 02385328, WO 02/008209, WO 02/014312, WO 02/46173, WO 02/48106, DE 10259786, WO 03/095438, U.S. Pat. No. 4,067,939 or WO 04/052869, by Novo Nordisk in EP 1532980, WO 03/055482, WO 04/002481, WO 05/049019, WO 05/066145 or WO 05/123132, by Merck/Banyu in WO 03/080585, WO 03/097824, WO 04/081001, WO 05/063738 or WO 05/090332, by Eli Lilly in WO 04/063194, or by Astra Zeneca in WO 01/020327, WO 03/000262, WO 03/000267, WO 03/015774, WO 04/045614, WO 04/046139, WO 05/044801, WO 05/054200, WO 05/054233, WO 05/056530, WO 05/080359, WO 05/080360 or WO 05/121110.

In one embodiment of the invention, the compound of the formula I is administered in combination with an inhibitor of gluconeogenesis, such as, for example, FR-225654.

In one embodiment of the invention, the compound of the formula I is administered in combination with inhibitors of fructose-1,6-bisphosphatase (FBPase), such as, for example, CS-917.

In one embodiment of the invention, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment of the invention, the compound of the formula I is administered in combination with inhibitors of glutamine-fructose-6-phosphate amidotransferase (GFAT), as are described for example in WO 2004/101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964X or as are described in WO 2003/074500, WO 2003/106456, WO 2004/50658, WO 2005/058901, WO 2005/012312, WO 2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of the formula I is administered in combination with inhibitors of 11-beta-hydroxysteroid dehydrogenase 1 (11β-HSD1), such as, for example, BVT-2733 or those as are described for example in WO 2001/90090-94, WO 2003/43999, WO 2004/112782, WO 2003/44000, WO 2003/44009, WO 2004/112779, WO 2004/113310, WO 2004/103980, WO 2004/112784, WO 2003/065983, WO 2003/104207, WO 2003/104208, WO 2004/106294, WO 2004/011410, WO 2004/033427, WO 2004/041264, WO 2004/037251, WO 2004/056744, WO 2004/065351, WO 2004/089367, WO 2004/089380, WO 2004/089470-71, WO 2004/089896, WO 2005/016877 or WO 2005/097759.

In one embodiment of the invention, the compound of the formula I is administered in combination with inhibitors of protein tyrosine phosphatase 1B (PTP1B), as are described for example in WO 2001/19830-31, WO 2001/17516, WO 2004/506446, WO 2005/012295, PCT/EP2005/005311, PCT/EP2005/005321, PCT/EP2005/007151, PCT/EP2005/01294 or DE 10 2004 060542.4.

In one embodiment of the invention, the compound of the formula I is administered in combination with modulators of the sodium-dependent glucose transporter 1 or 2 (SGLT1, SGLT2), such as, for example, KGA-2727, T-1095 and SGL-0010 or as are described for example in WO 2004/007517, WO 2004/52903, WO 2004/52902, WO 2005/121161, WO 2005/085237, JP2004359630 or by A. L. Handlon in Expert Opin. Ther. Patents (2005) 15(11), 1531-1540.

In one embodiment of the invention, the compound of the formula I is administered in combination with inhibitors of hormone-sensitive lipase (HSL) as described for example in WO 01/17981, WO 01/66531, WO 2004/035550, WO 2005/073199 or WO 03/051842.

In one embodiment of the invention, the compound of the formula I is administered in combination with inhibitors of acetyl-CoA carboxylase (ACC), such as, for example, those as described in WO 1999/46262, WO 2003/72197, WO 2003/072197 or WO 2005/044814.

In one embodiment of the invention, the compound of the formula I is administered in combination with an inhibitor of phosphoenolpyruvate carboxykinase (PEPCK), such as, for example, those as described in WO 2004/074288.

In one embodiment of the invention, the compound of the formula I is administered in combination with an inhibitor of glycogen synthase kinase 3 beta (GSK-3 beta), as described for example in US2005222220, WO 2004/046117, WO 2005/085230, WO 2005/111018, WO 2003/078403, WO 2004/022544, WO 2003/106410, WO 2005/058908, US2005038023, WO 2005/009997, US2005026984, WO 2005/000836, WO 2004/106343, EP1460075, WO 2004/014910, WO 2003/076442, WO 2005/087727 or WO 2004/046117.

In one embodiment of the invention, the compound of the formula I is administered in combination with an inhibitor of protein kinase C beta (PKC beta), such as, for example, ruboxistaurin.

In one embodiment of the invention, the compound of the formula I is administered in combination with an endothelin A receptor antagonist such as, for example, avosentan (SPP-301).

In one embodiment of the invention, the compound of the formula I is administered in combination with inhibitors of "I-kappaB kinase" (IKK inhibitors), as are described for example in WO 2001/000610, WO 2001/030774, WO 2004/022553 or WO 2005/097129.

In one embodiment of the invention, the compound of the formula I is administered in combination with modulators of the glucocorticoid receptor, like those described for example in WO 2005/090336.

In a further embodiment of the invention, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558); NPY antagonists such as, for example, naphthalene-1-sulfonic acid {4-[(4-amino-quinazolin-2-ylamino)methyl]cyclohexylmethyl}amide hydrochloride (CGP 71683A); peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO 2005/080424;

cannabinoid receptor 1 antagonists such as, for example, rimonabant, SR147778 or those as are described for example in EP 0656354, WO 00/15609, WO 02/076949, WO 2005/080345, WO 2005/080328, WO 2005/080343, WO 2005/075450, WO 2005/080357, WO 2001/70700, WO 2003/026647-48, WO 2003/02776, WO 2003/040107, WO 2003/007887, WO 2003/027069, U.S. Pat. No. 6,509,367, WO 2001/32663, WO 2003/086288, WO 2003/087037, WO 2004/048317, WO 2004/058145, WO 2003/084930, WO 2003/084943, WO 2004/058744, WO 2004/013120, WO 2004/029204, WO 2004/035566, WO 2004/058249, WO 2004/058255, WO 2004/058727, WO 2004/069838, US20040214837, US20040214855, US20040214856, WO 2004/096209, WO 2004/096763, WO 2004/096794, WO 2005/000809, WO 2004/099157, US20040266845, WO 2004/110453, WO 2004/108728, WO 2004/000817, WO 2005/000820, US20050009870, WO 2005/00974, WO 2004/111033-34, WO 2004/11038-39, WO 2005/016286, WO 2005/007111, WO 2005/007628, US20050054679, WO 2005/027837, WO 2005/028456, WO 2005/063761-62, WO 2005/061509 or WO 2005/077897;

MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those as are described in WO 2005/060985, WO 2005/009950, WO 2004/087159, WO 2004/078717, WO 2004/078716, WO 2004/024720, US20050124652, WO 2005/051391, WO 2004/112793, WOUS20050222014, US20050176728, US20050164914, US20050124636, US20050130988, US20040167201, WO 2004/005324, WO 2004/037797, WO 2005/042516, WO 2005/040109, WO 2005/030797, US20040224901, WO 2005/01921, WO 2005/09184, WO 2005/000339, EP1460069, WO 2005/047253, WO 2005/047251, EP1538159, WO 2004/072076, WO 2004/072077 or WO 2006/024390;

orexin receptor antagonists (e.g. 1-(2-methylbenzoxazol-6-yl)-3-[1,5]naphthyridin-4-ylurea hydrochloride (SB-334867-A) or those as are described for example in WO 2001/96302, WO 2001/85693, WO 2004/085403 or WO 2005/075458); histamine H3 receptor agonists (e.g. 3-cyclohexyl-1-(4,4-dimethyl-1,4,6,7-tetrahydro-imidazo[4,5-c]pyridin-5-yl)propan-1-one oxalic acid salt (WO 00/63208) or those as are described in WO 2000/64884, WO 2005/082893);

CRF antagonists (e.g. [2-methyl-9-(2,4,6-trimethylphenyl)-9H-1,3,9-triazafluoroen-4-yl]dipropylamine (WO 00/66585));

CRF BP antagonists (e.g. urocortin);

urocortin agonists;

β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO 2003/15769, WO 2005/085200, WO 2005/019240, WO 2004/011438, WO 2004/012648, WO 2003/015769, WO 2004/072025, WO 2005/070898, WO 2005/070925, WO 2006/018280, WO 2006/018279, WO 2004/039780, WO 2003/033476, WO 2002/006245, WO 2002/002744, WO 2003/004027 or FR2868780);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (e.g. dexfenfluramine);

mixed serotoninergic and noradrenergic compounds (e.g. WO 00/71549);

5-HT receptor agonists, e.g. 1-(3-ethylbenzofuran-7-yl)piperazine oxalic acid salt (WO 01/09111);

5-HT2C receptor agonists (such as, for example, APD-356, BVT-933 or those as are described in WO 2000/77010, WO 2007/7001-02, WO 2005/019180, WO 2003/064423, WO 2002/42304 or WO 2005/082859);

5-HT6 receptor antagonists as are described for example in WO 2005/058858;

bombesin receptor agonists (BRS-3 agonists);

galanin receptor antagonists;

growth hormone (e.g. human growth hormone or AOD-9604);

growth hormone releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO 2005/030734;

TRH agonists (see, for example, EP 0 462 884);

uncoupling protein 2 or 3 modulators;

leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (like those described for example in WO 00/40569);

inhibitors of diacylglycerol O-acyltransferases (DGATs) as described for example in US2004/0224997, WO 2004/094618, WO 2000/58491, WO 2005/044250, WO 2005/072740, JP2005206492 or WO 2005/013907;

inhibitors of fatty acid synthase (FAS) such as, for example, C75 or those as described in WO 2004/005277;

oxyntomodulin;

oleoyl-estrone or thyroid hormone receptor agonists such as, for example: KB-2115 or those as described in WO 2005/8279, WO 2001/72692, WO 2001/94293, WO 2003/084915, WO 2004/018421 or WO 2005/092316.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindole or phentermine.

In one embodiment of the invention, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6)). Caromax is a carob-containing product from Nutrinova, Nutrition Specialties & Food Ingredients GmbH, Industriepark Hoechst, 65926 Frankfurt/Main. Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compound of the formula I is administered in combination with PDE inhibitors (phosphodiesterase), like those described for example in WO 2003/077949 or WO 2005/012485.

In one embodiment of the invention, the compound of the formula I is administered in combination with NAR-1 (nicotinic acid receptor) agonists like those described for example in WO 2004/094429.

In one embodiment of the invention, the compound of the formula I is administered in combination with CB2 (cannabinoid receptor) agonists like those described for example in US2005/143448.

In one embodiment of the invention, the compound of the formula I is administered in combination with histamine 1 agonists like those described for example in WO 2005/101979.

In one embodiment of the invention, the compound of the formula I is administered in combination with bupropion as described in WO 2006/017504.

In one embodiment of the invention, the compound of the formula I is administered in combination with opioid antagonists like those described for example in WO 2005/107806 or WO 2004/094429.

In one embodiment of the invention, the compound of the formula I is administered in combination with neutral endopeptidase inhibitors like those described for example in WO 2002/02513, WO 2002/06492, WO 2002/040008, WO 2002/040022 or WO 2002/047670.

In one embodiment of the invention, the compound of the formula I is administered in combination with NPY inhibitors (neuropeptide Y) like those described for example in WO 2002/047670.

In one embodiment of the invention, the compound of the formula I is administered in combination with sodium/hydrogen exchange inhibitors like those described for example in WO 2003/092694.

In one embodiment of the invention, the compound of the formula I is administered in combination with modulators of the glucocorticoid receptor like those described for example in WO 2005/090336.

In one embodiment of the invention, the compound of the formula I is administered in combination with nicotine receptor agonists like those described for example in WO 2004/094429.

In one embodiment of the invention, the compound of the formula I is administered in combination with NRIs (norepinephrine reuptake inhibitors) like those described for example in WO 2002/053140.

In one embodiment of the invention, the compound of the formula I is administered in combination with MOA (E-beta-methoxyacrylate) such as, for example, segeline or like those described for example in WO 2002/053140.

In one embodiment of the invention, the compound of the formula I is administered in combination with antithrombotic active ingredients such as, for example, clopidogrel.

It will be appreciated that every suitable combination of the compounds of the invention with one or more of the aforementioned compounds and optionally one or more other pharmacologically active substances is regarded as falling within the protection conferred by the present invention.

Some of the formulae for the development codes mentioned above are detailed hereinafter.

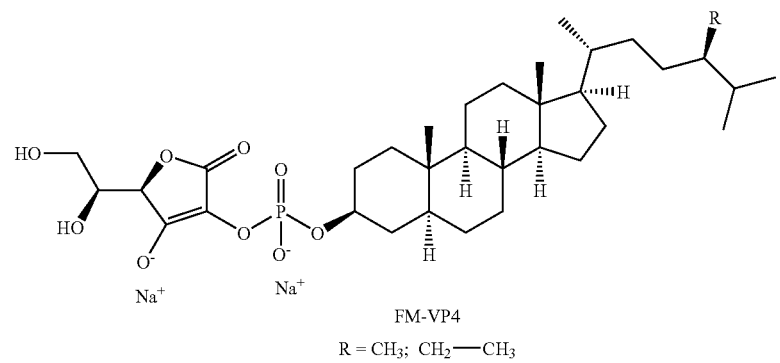

FM-VP4
R = CH₃; CH₂—CH₃

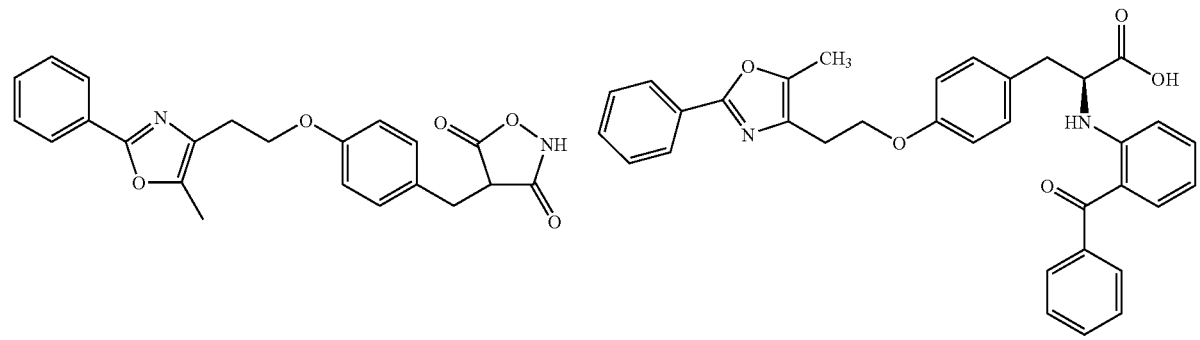

JTT-501

GI 262570

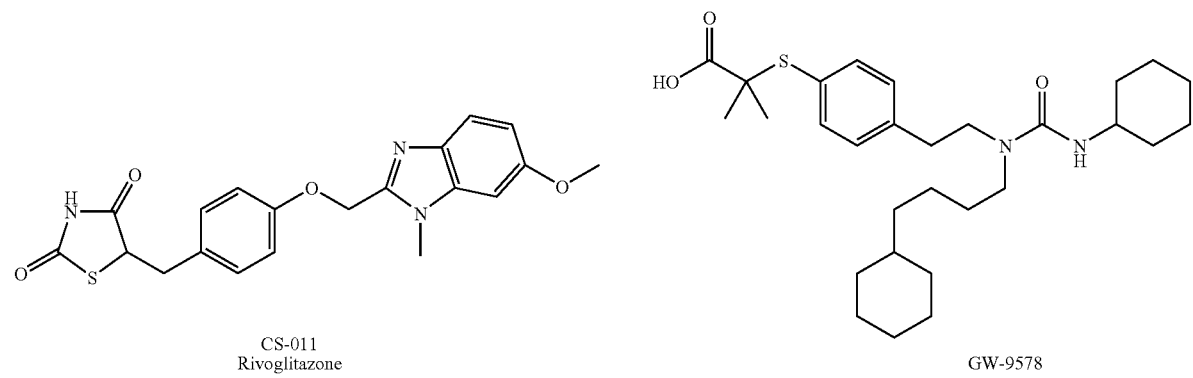

CS-011
Rivoglitazone

GW-9578

-continued
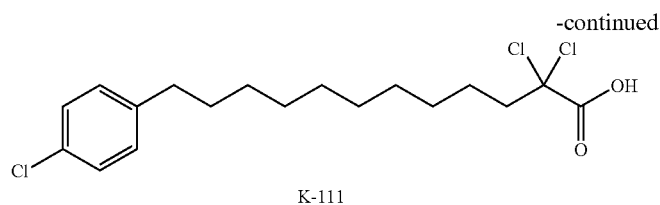
K-111
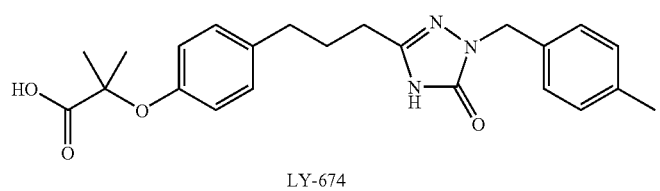
LY-674
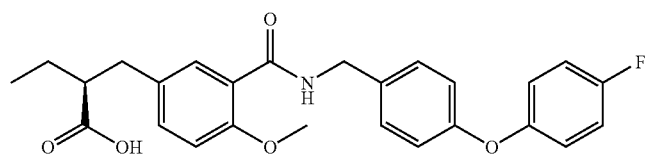
KRP-101
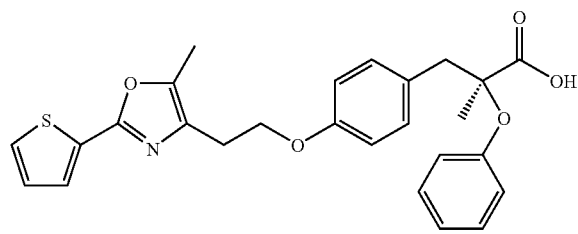
LY-510929
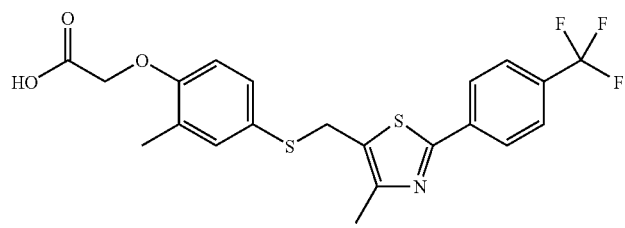
GW-501516
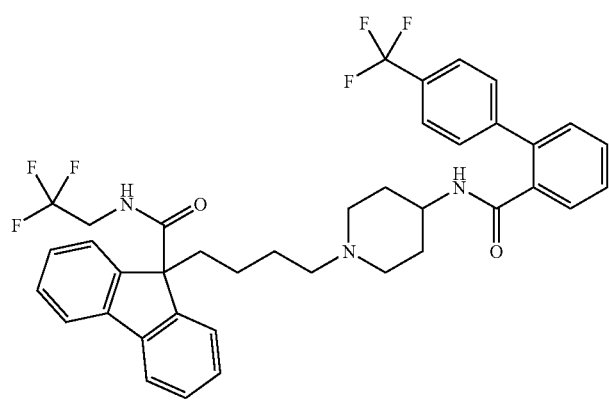
BMS-201038

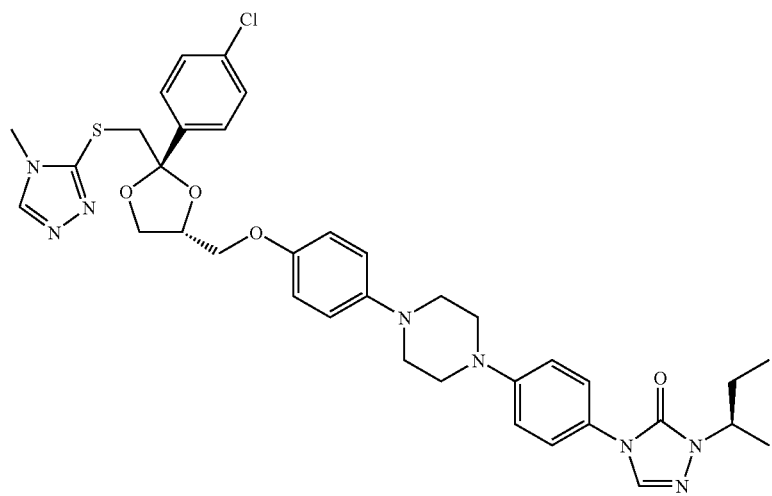
R-103757
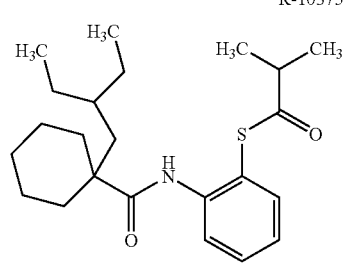
JTT-705
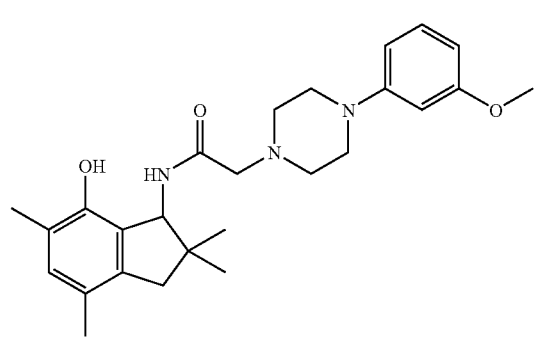
OPC-14117
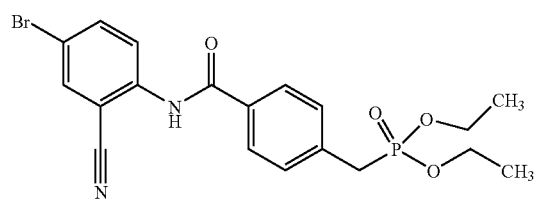
NO-1886
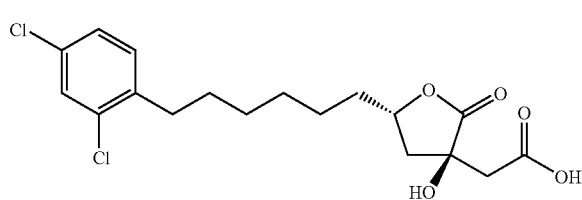
SB-204990
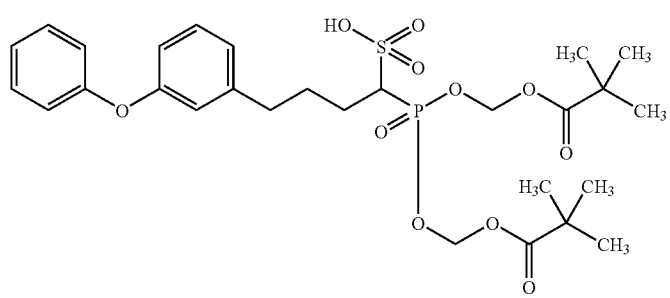
BMS-188494
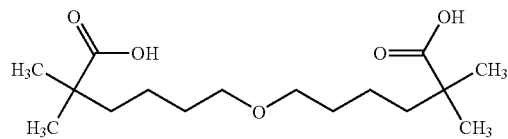
CI-1027
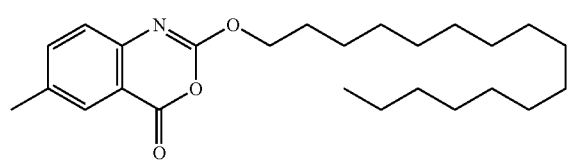
ATL-962

-continued
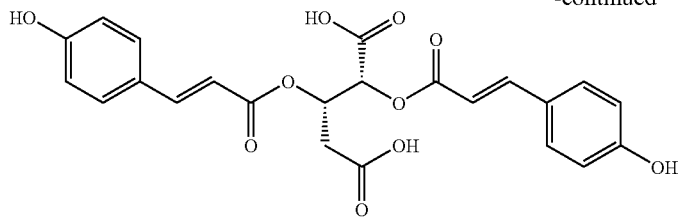
FR-258900
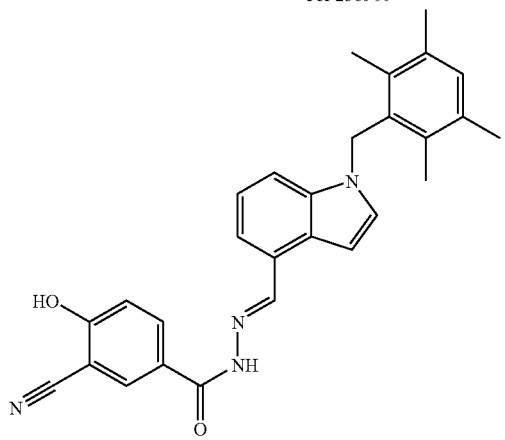
NNC-25-2504
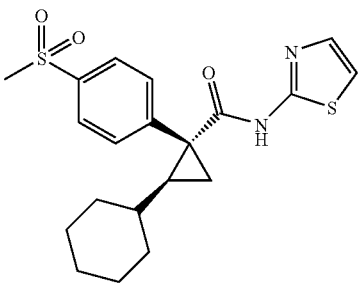
LY-2121260
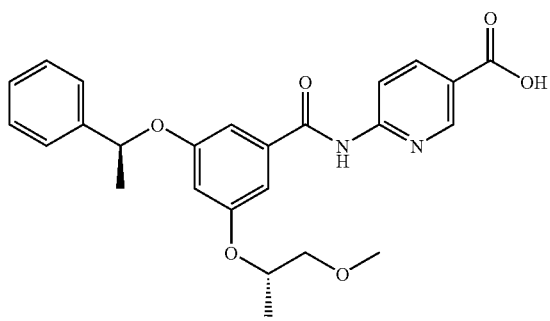
GKA-50
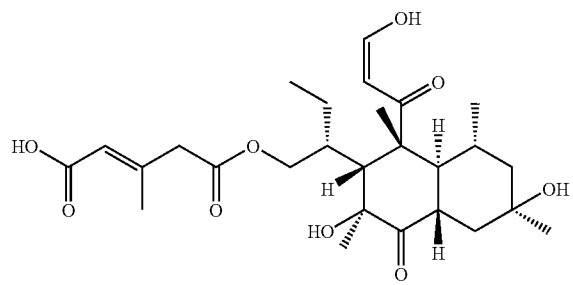
FR-225654
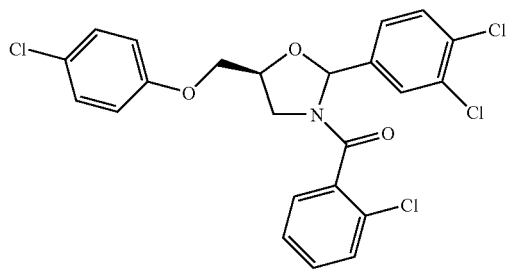
KST-48
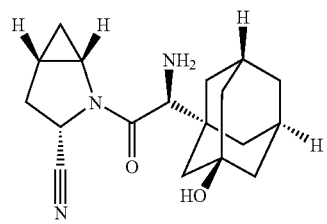
BMS-477118
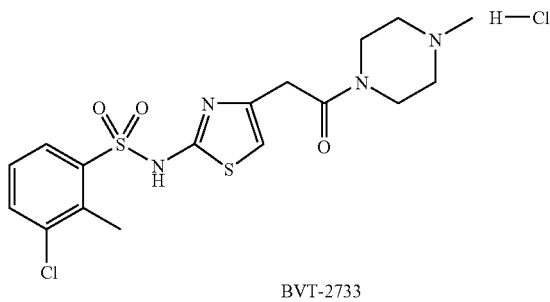
BVT-2733
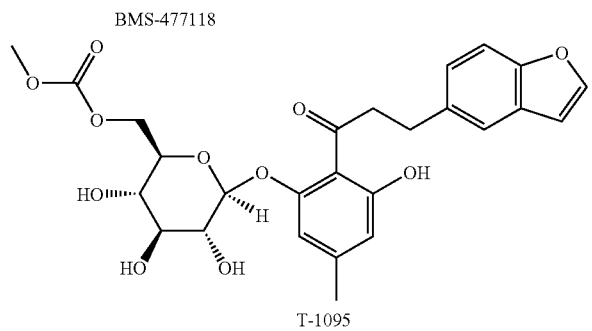
T-1095

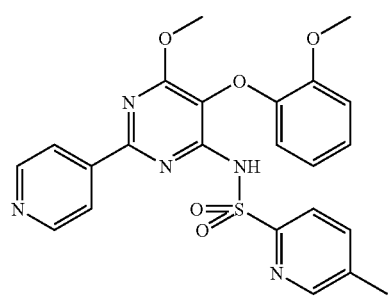
SPP-301
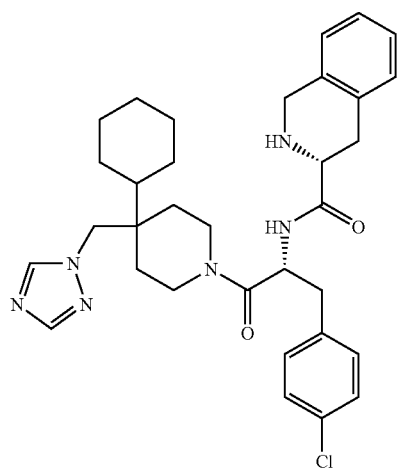
THIQ
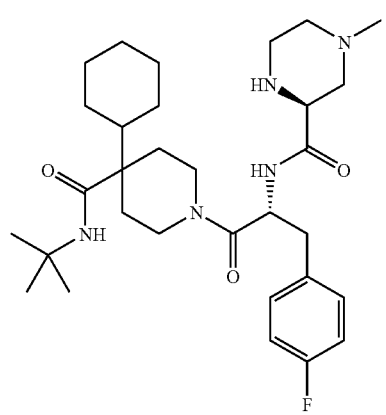
MB243
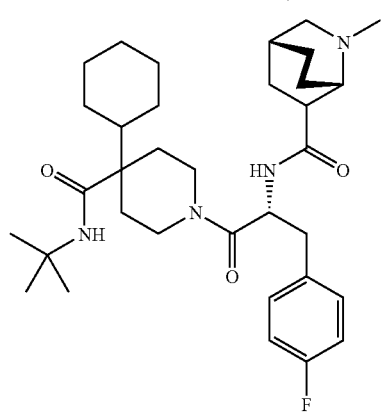
RY764
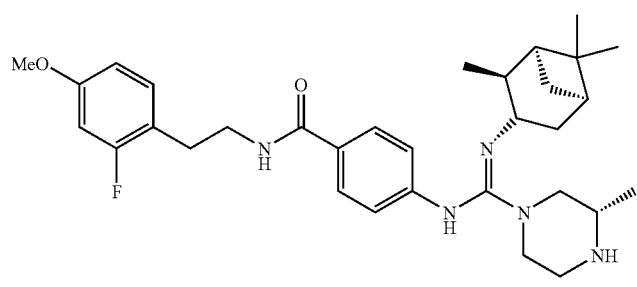
CHIR-785
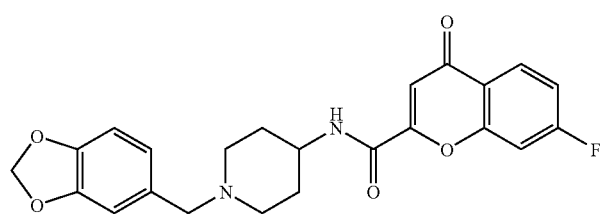
A-761
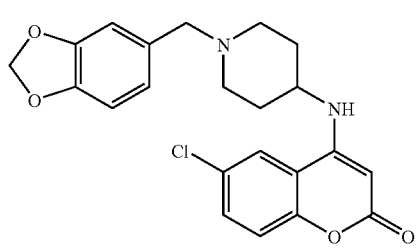
A-665798

-continued
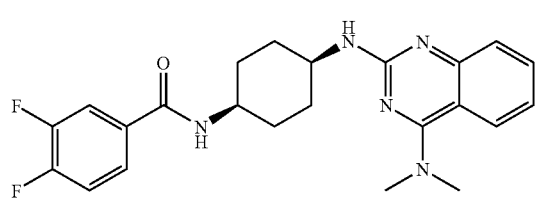
ATC-0175
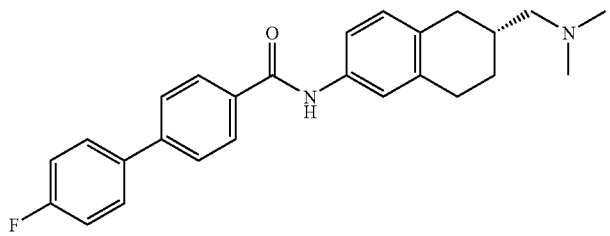
T-226296
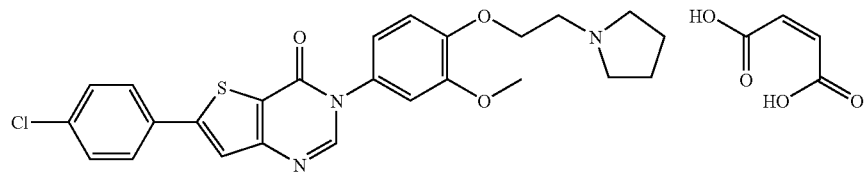
GW-803430
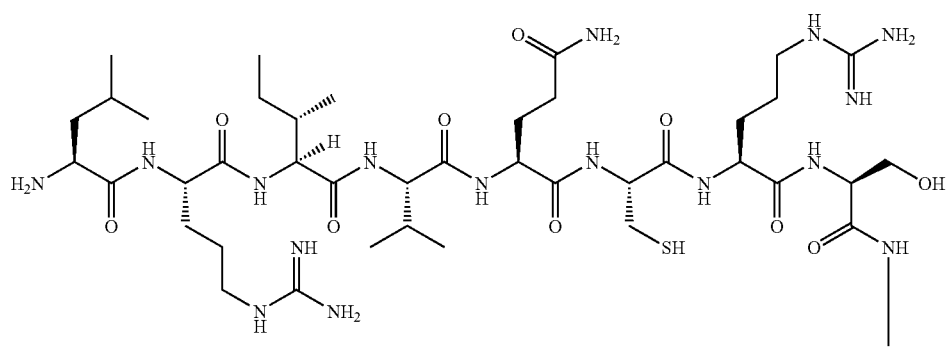
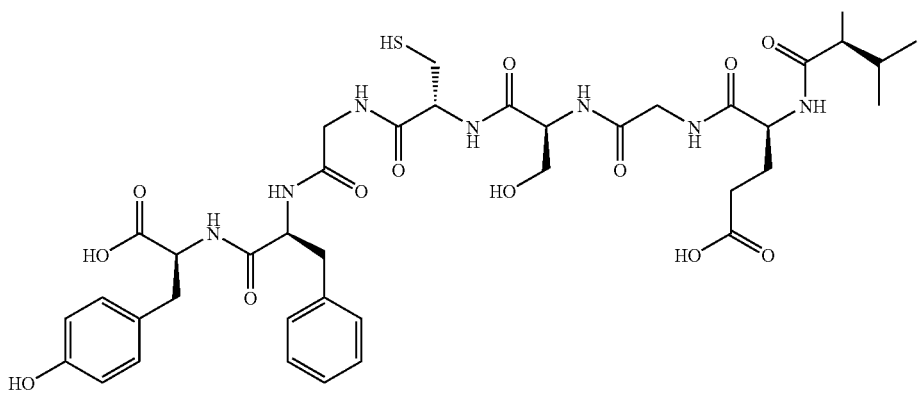
AOD-9604
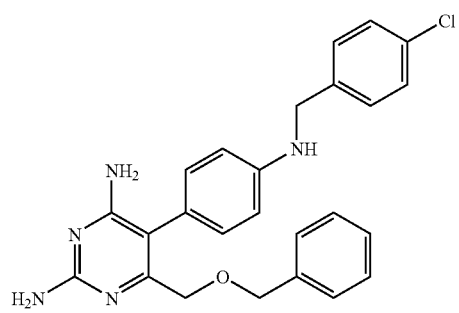
A-778193
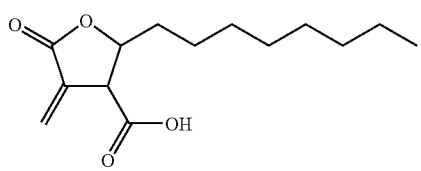
C75

-continued

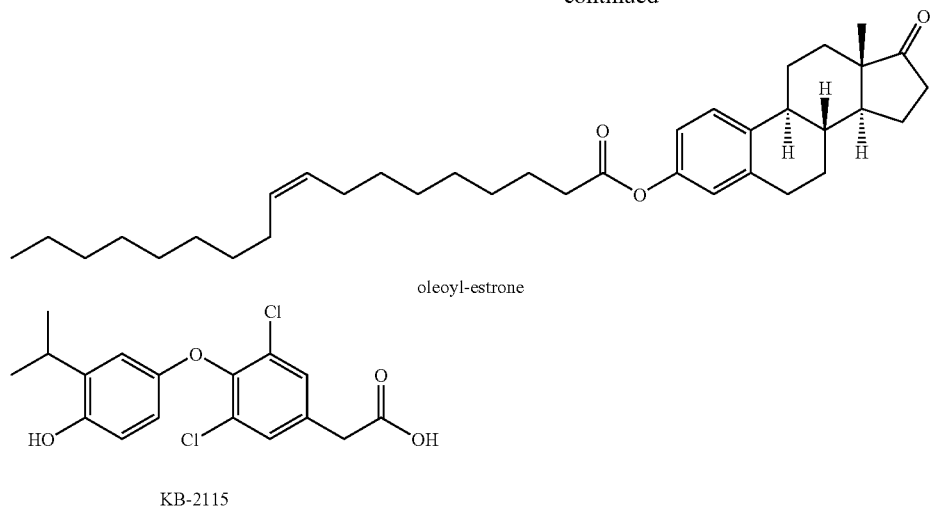

oleoyl-estrone

KB-2115

Pharmacological Testing

The activity of the compounds of the invention of the formula I was tested in the following enzyme assay systems:
EL Inhibition Assay:
Preparation of EL EL is released as secretory protein in high concentration into cell culture medium (conditioned medium) by recombinant cell lines (CHO, HEK293). This was employed as enzyme solution after concentration.
EL Activity Assay The phospholipase-specific substrate 1,2-bis(4,4-difluoro-5,7-dimethyl-4-bora-3a,4a-diaza-s-indacene-3-undecanoyl)-sn-glycero-3-phosphocholine, (manufacturer Molecular Probes) was used to characterize the enzymatic activity of endothelial lipase and the effect of inhibitors. Hydrolysis of the A1 ester linkage of this phospholipid by the enzyme liberates a fatty acid labeled with the fluorescent dye Bodipy which can be detected after separation by thin-layer chromatography on an HPTLC plate (silica gel 60, Merck) or directly in the reaction vessel by measuring the fluorescence.

The substrate solution was prepared by 100 µg of 1,2-bis (4,4-difluoro-5,7-dimethyl-4-bora-3a,4a-diaza-s-indacene-3-undecanoyl)-sn-glycero-3-phospho-choline (manufacturer Molecular Probes) being dissolved in 100 µl of DMSO and taken up with 2.4 mg of tripalmitin (Sigma) in 393 µl of chloroform which contained 20 mg/ml DOP-choline (1,2-dioleoyl-sn-glycero-3-phosphocholine). 39.3 µl of this lipid mixture were transferred into a fresh reaction vessel and the solvent was evaporated. The lipid mixture was dissolved in 4 ml of 200 mM TRIS-HCl, 150 mM sodium chloride, pH=7.4, by sonication twice. The subsequent enzymic reaction took place at 37° C. for 90 minutes. For this purpose, 20 µl of the substrate solution were incubated with 2 µl of inhibitor of appropriate concentration (dissolved in 10% DMSO, using 10% DMSO solution for control) and 2 µl of enzyme solution (conditioned medium). Then 4 µl of the assay mixture were loaded onto an HPTLC plate (silica gel 60, Merck), and the liberated fluorescent dye was separated for detection with an eluent (diethyl ether:petroleum benzene:acetic acid [78:22:1]). After evaporation of the eluent, the plate was read in a fluorescence scanner. An increased liberation of the fluorescent dye in the uninhibited reaction was to be observed as a measure of the enzymic activity.

The enzymatic activity was reduced as a function of the inhibitor concentration used. The inhibitor concentration at which a half-maximum enzymatic activity is observed is called $IC_{50}$.

In this assay, the compounds of the examples showed the following $IC_{50}$ values:

| Example | $IC_{50}$ [µM] EL |
| --- | --- |
| 2 | 0.02 |
| 4 | 0.019 |
| 6 | 0.043 |
| 8 | 0.091 |
| 9 | 1.21 |
| 10 | 0.001 |
| 11 | 1.231 |
| 12 | 0.029 |
| 13 | 0.204 |
| 14 | 0.008 |
| 15 | 0.057 |
| 16 | 0.01 |
| 17 | 0.011 |

Other Test Models

Suitability of the compounds of the invention as active pharmaceutical ingredient can be tested by means of various test models. Descriptions are given of such test models by way of example below.
Solubility in Aqueous Systems Adequate solubility of a substance in aqueous solvent systems is an important prerequisite for a (reproducible) pharmacological effect. Solubilities in aqueous systems can be determined by various methods. Suitable examples of solution precipitation methods ("kinetic solubility") and methods which investigate the dissolution of a solid sample until an equilibrium is set up ("thermodynamic solubility").
a) Kinetic Solubility A DMSO solution of the test compound (2.5 mM; 0.5 µL) is pipetted into 200 µL of an aqueous test solution (e.g. phosphate-buffered saline, 10×, 1M, Sigma, adjusted to 10 mM, pH 7.4) in a 96-well microtiter plate, and the turbidity is measured at the resulting theoretical concentration for the test compound of 6.25 µM using a nephelometer (e.g. Nephelostar Galaxy, BMG Labtech). The concentration of the test compound in the aqueous test solution is then raised to a theoretical 12.5 µM by adding further DMSO solution (2.5 mM; 0.5 µL), and the turbidity measurement is repeated. Further additions of DMSO solutions (1 µL, 2.5 mM; 0.5 µL, 10 mM; then 9×1 µL, 10 mM resulting in theoretical concentrations of 25 µM, 50 µM, 100 µM, 150 µM, 200 µM, 250 µM, 300 µM, 350 µM, 400 µM, 450 µM and 500 µM) with turbidity measurement in between complete the measurement process.

Evaluation: The turbidity values from the nephelometer are plotted against the theoretical concentration of the test compound in the aqueous test solution. As soon as a significant turbidity is detected (e.g. 5 times above the control value of the aqueous test solution) at a theoretical concentration, the level of concentration below this is stated to be the solubility limit of the test compound in the test solution. Thus, the maximum possible measurement range emerges as values<6.25 µM, 6.25-500 µM and >500 µM.

Preferred compounds of the invention show a kinetic solubility in phosphate buffer (pH 7.4) of at least 12.5 µM; more preferably of at least 50 µM and even more preferably of at least 250 µM.

b) Thermodynamic Solubility

The integrated UV absorption from HPLC UV measurement of serial dilutions of the test compound in DMSO (500 µM, 100 µM, 50 µM, 10 µM and 1 µM) shows a linear correlation with the concentration in a calibration line. The test compound (500 µg) is shaken together with the aqueous test solution (250 µL) in a closed vessel (capacity: 1.5 mL) for 16 hours (Eppendorf thermoshaker, 1400 rpm, 25° C., covering to protect from light). The sample is then centrifuged at maximum rotational speed, and the supernatant is finally filtered. A sample of the filtered supernatant is analyzed directly by HPLC UV measurement (see above). A further sample is analyzed after dilution (1 part by volume of supernatant, 39 parts by volume of test solution).

Evaluation: The concentration of the test compound in the undiluted supernatant is calculated from the resulting integrated UV absorptions of the supernatant samples on the basis of the constructed calibration lines and stated as solubility of the test compound in the respective aqueous test solution.

Examples of aqueous test solutions are deionized water or aqueous phosphate buffer with various pH values (e.g. pH 1.2; pH 4.0; pH 6.8; pH 7.4; pH 9.0) which can be prepared from the commercial solution (phosphate buffered saline, 10×, Sigma) by dilution and adjustment with phosphoric acid or sodium hydroxide solution by standard methods.

Preferred compounds of the invention show a solubility in phosphate buffer (pH 7.4) of at least 12.5 µM; more preferably of at least 50 µM and even more preferably of at least 250 µM.

Metabolic Stability

The metabolic stability is determined by incubating the test compound (5 µM) with microsomal liver fractions (1 mg/mL protein with 0.1% w/v BSA; 1 mM NADPH, 0.5% DMSO) at 37° C. Analysis at an incubation time of 0 and 20 minutes takes place by means of LCMS/MS. Further descriptions of the test system and references for the experimental procedure are to be found in Plant, N.; Drug Discovery Today 2004, 9(7), 328-336 and Lau, Y. Y. et al.; Pharmaceutical Res. 2002, 19(11), 1606-1610.

Preparation Processes

The compounds of the invention of the general formula I are prepared by methods known per se, e.g. by acylation of substituted or unsubstituted azolopyridin-3-ol derivatives II. The azolopyridin-3-ol derivatives II can be reacted with the corresponding isocyanates III to give I (method A).

On the other hand, the azolopyridin-3-ol derivatives 11 can be reacted with carbamoyl chlorides VI (method B), or in two stages by reacting azoles II with phosgene or equivalents such as trichloromethyl chlorocarbonate, ditrichloromethyl carbonate or 4-nitrophenyl chloroformate and further reaction of the resulting azolecarboxylic acid derivative with amines VII (method C).

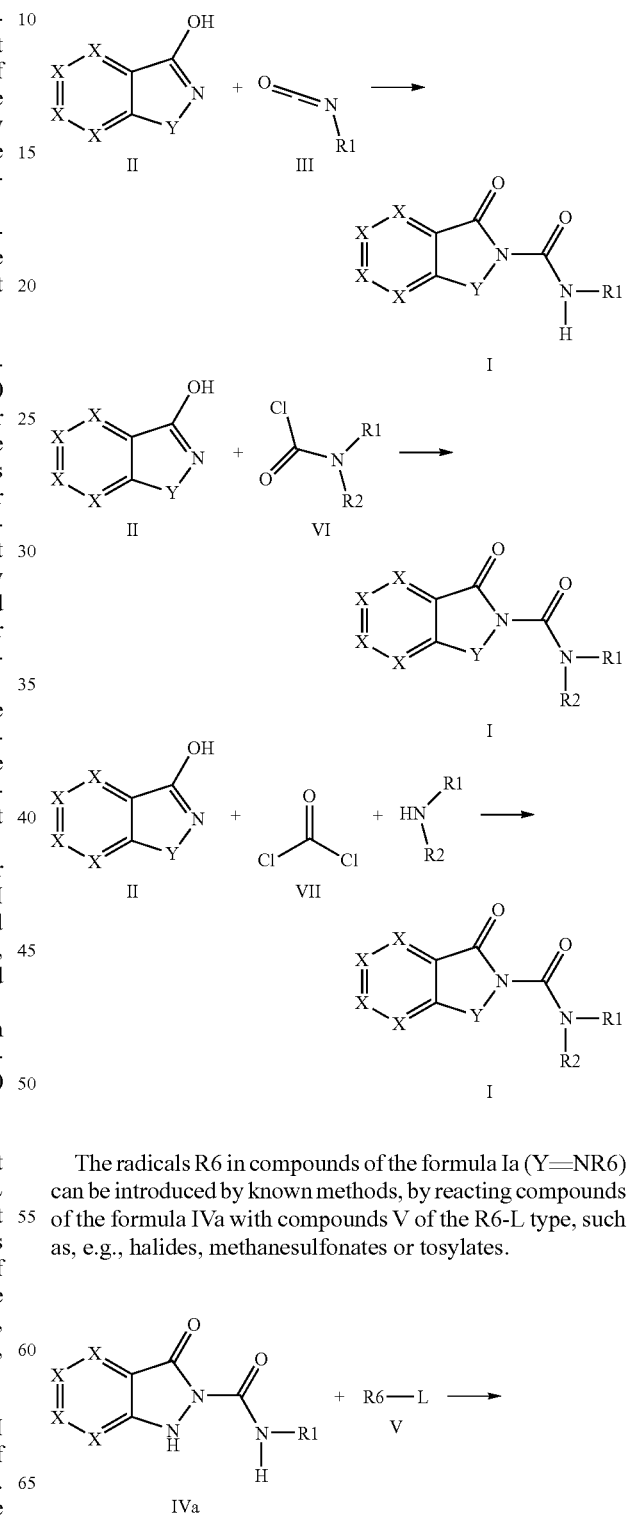

The radicals R6 in compounds of the formula Ia (Y=NR6) can be introduced by known methods, by reacting compounds of the formula IVa with compounds V of the R6-L type, such as, e.g., halides, methanesulfonates or tosylates.

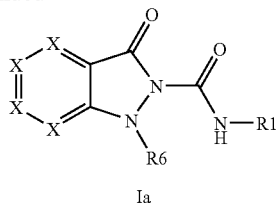

Since acids are usually liberated in these reactions, it is advisable to add bases such as pyridine, triethylamine, sodium hydroxide solution or alkali metal carbonates for expedition. The reactions can be carried out in wide temperature ranges. It has usually proved to be advantageous to operate at from 0° C. to the boiling point of the solvent used. Examples of solvents employed are methylene chloride, THF, DMF, toluene, ethyl acetate, n-heptane, dioxane, diethyl ether or pyridine. If anhydrous conditions are used, strong bases such as lithium hydride, sodium hydride or potassium tert-butoxide in aprotic solvents such as THF or DMF have also proved suitable.

The azolopyridin-3-ol derivatives II employed as starting compounds are commercially available or can be prepared by processes known from the literature (e.g. L. Baiocchi, G. Corsi Synthesis (1978) 633-648; I. Sekikawa et al. J. Het. Chem. (1973) 931-932; A. Dornow, M. Siebrecht, Chem. Ber. (1960) 1106-1110; M. Tilser, B. Stanovnik, Z. Zrimsek, Heterocycles (1979) 217-219; K. Bowden, G. Crank, W. J. Roos, J. Chem. Soc. 1968, 172-185).

The examples detailed below serve to illustrate the invention without, however, restricting it.

EXAMPLES

Example 1

6-Chloro-4-methyl-3-oxo-1,3-dihydropyrazolo[3,4-b]pyridin-2-carboxylic acid 2-methylbenzylamide a) 4-Methyl-1H-pyrazolo[3,4-b]pyridine-3,6-diol 20 g (201.8 mmol) of 5-amino-2H-pyrazol-3-ol and 26 g (224 mmol) of methyl 3-oxo-butyrate were heated under reflux in 63 ml of conc. hydrochloric acid and 17 ml of water for 1 h. After cooling, the product crystallized and was filtered off with suction and dried. Yield: 16.54 g (50%), M+H+: 166.07.

b) 6-Chloro-4-methyl-1H-pyrazolo[3,4-b]pyridin-3-ol 2.5 g (15.14 mmol) of 4-methyl-1H-pyrazolo[3,4-b]pyridine-3,6-diol and 4.75 ml (39.2 mmol) of N,N-dimethylaniline were cautiously added to 60 ml of phosphorus oxychloride and the mixture was stirred at 115° C. for 5 h. The reaction mixture was concentrated and hydrolyzed with 30 g of ice. The product crystallized after some time. It was filtered off with suction and dried. Yield: 1.77 g (64%), M+H+: 184.1.

c) 6-Chloro-4-methyl-3-oxo-1,3-dihydropyrazolo[3,4-b]pyridine-2-carboxylic acid 2-methylbenzylamide 136 µl (0.98 mmol) of 2-methylbenzyl isocyanate were added to 150 mg (0.82 mmol) of 6-chloro-4-methyl-1H-pyrazolo[3,4-b]pyridin-3-ol in 10 ml of THF and 2 ml of DMF at room temperature. The reaction mixture was stirred at room temperature for 2 h and left to stand overnight. Concentration was followed by purification by preparative HPLC (PR18, acetonitrile/water 0.1% TFA). Yield: 139 mg (51%), M+H+: 331.18.

Example 2

6-Chloro-1,4-dimethyl-3-oxo-1,3-dihydro-pyrazolo[3,4-b]pyridine-2-carboxylic acid 2-methylbenzylamide 99.89 mg (0.3 mmol) of 6-chloro-4-methyl-3-oxo-1,3-dihydropyrazolo[3,4-b]pyridine-2-carboxylic acid 2-methylbenzylamide and 37.3 mg (0.33 mmol) of potassium tert-butoxide were stirred in 10 ml of THF at room temperature for 10 minutes. Addition of 20.7 µl of iodomethane was followed by stirring at room temperature for 2 h and at 60° C. for 4 h. Then 30 µl of iodomethane and 50 µl of triethylamine were added, and stirring was continued at 60° C. for 7 h, the mixture was concentrated and mixed with water and ethyl acetate, and the organic phase was separated off, concentrated and purified by preparative HPLC (PR18, acetonitrile/water 0.1% TFA). Yield: 18 mg (17%), M+H+: 345.08.

Example 3

6-Chloro-4-methyl-3-oxo-1,3-dihydropyrazolo[3,4-b]pyridine -2-carboxylic acid (2-thiophen-2-yiethyl)amide In analogy to example 1c, 200 mg (1.09 mmol) of 6-chloro-4-methyl-1H-pyrazolo-[3,4-b]pyridin-3-ol were reacted with 183.5 mg (1.19 mmol) of 2-(2-isocyanatoethyl)-thiophene in THF at room temperature. Yield: 184 mg (50%), M+H+: 337.09.

Example 4

6-Chloro-1,4-dimethyl-3-oxo-1,3-dihydropyrazolo[3,4-b]pyridine-2-carboxylic acid (2-thiophen-2-yl-ethyl)amide In analogy to example 2, 100 mg (0.297 mmol) of 6-chloro-4-methyl-3-oxo-1,3-dihydropyrazolo[3,4-b]pyridine-2-carboxylic acid (2-thiophen-2-ylethyl)amide were reacted with 22.2 µl of iodomethane in THF. Yield: 18 mg (77%), M+H+: 351.12.

Example 5

6-Chloro-4-methyl-3-oxo-1,3-dihydropyrazolo[3,4-b]pyridine -2-carboxylic acid hexylamide In analogy to example 1c, 500 mg (2.72 mmol) of 6-chloro-4-methyl-1H-pyrazolo-[3,4-b]pyridin-3-ol were reacted with 346.3 mg (2.72 mmol) of 1-isocyanatohexane in THF at 60° C. Yield: 428 mg (51%), M+H+: 311.27.

Example 6

3-Oxo-3H-isoxazolo[5,4-b]pyridine-2-carboxylic acid hexylamide

In analogy to example 1c, 100 mg (0.735 mmol) of isoxazolo[5,4-b]pyridin-3-ol were reacted with 112.2 mg (0.88 mmol) of 1-isocyanatohexane in THF at RT. Yield: 100 mg (52%), M+H+: 264.1.

Example 7

6-Chloro-4-methyl-3-oxo-1,3-dihydropyrazolo[3,4-b]pyridine-2-carboxylic acid (S)-indan-1-ylamide In analogy to example 1c, 200 mg (1.089 mmol) of 6-chloro-4-methyl-1H-pyrazolo-[3,4-b]pyridin-3-ol were reacted with 208.1 mg (1.2 mmol) of (S)-1-isocyanatoindane in THF/DMF at RT. Yield: 153 mg (41%), M+H+: 343.32.

Example 8

6-Chloro-4-methyl-3-oxo-1,3-dihydropyrazolo[3,4-b]pyridine-2-carboxylic acid (R)-indan-1-ylamide In analogy to example 1c, 200 mg (1.089 mmol) of 6-chloro-4-methyl-1H-pyrazolo-[3,4-b]pyridin-3-ol were reacted with 208.1 mg (1.2 mmol) of (R)-1-isocyanatoindane in THF/DMF at RT. Yield: 154 mg (41%), M+H+: 343.32.

Example 9

6-Chloro-4-methyl-3-oxo-1,3-dihydropyrazolo[3,4-b]pyridine-2-carboxylic acid (1,2,3,4-tetrahydronaphthalen-1-yl)amide In analogy to example 1c, 200 mg (1.089 mmol) of 6-chloro-4-methyl-1H-pyrazolo-[3,4-b]pyridin-3-ol were reacted with 226.4 mg (1.2 mmol) of 1-isocyanato-1,2,3,4-tetrahydronaphthalene in THF/DMF at RT. Yield: 142 mg (37%), M+H+: 357.35.

Example 10

1-Butyl-6-chloro-4-methyl-3-oxo-1,3-dihydropyrazolo[3,4-b]pyridine-2-carboxylic acid hexylamide In analogy to example 2, 100 mg (0.32 mmol) of 6-chloro-4-methyl-3-oxo-1,3-dihydropyrazolo[3,4-b]pyridine-2-carboxylic acid hexylamide were reacted with 59.2 mg (0.32 mmol) of 1-iodobutane in DMF with triethylamine at RT. Yield: 23 mg (19%), M+H+: 367.27.

Example 11

1-Butyl-6-chloro-4-methyl-3-oxo-1,3-dihydropyrazolo[3,4-b]pyridine-2-carboxylic acid (2-thiophen-2-ylethyl)amide In analogy to example 2, 50 mg (0.148 mmol) of 6-chloro-4-methyl-3-oxo-1,3-dihydropyrazolo[3,4-b]pyridine-2-carboxylic acid (2-thiophen-2-ylethyl)amide were reacted with 41 mg (0.22 mmol) of 1-iodobutane in DMF with sodium hydride. Yield: 8 mg (14%), M+H+: 393.47

Example 12

6-Chloro-1,4-dimethyl-3-oxo-1,3-dihydropyrazolo[3,4-b]pyridine-2-carboxylic acid (1,2,3,4-tetrahydronaphthalen-1-yl)amide In analogy to example 2, 50 mg (0.14 mmol) of 6-chloro-4-methyl-3-oxo-1,3-dihydro-pyrazolo[3,4-b]pyridine-2-carboxylic acid (1,2,3,4-tetrahydronaphthalen-1-yl)amide were reacted with 23.85 mg (0.168 mmol) of iodomethane in DMF with 2,3,4,6,7,8,9,10-octahydropyrimido[1,2-a]azepine (DBU) at RT. Yield: 12 mg (23%), M+H+: 371.42.

Example 13

6-Chloro-1,4-dimethyl-3-oxo-1,3-dihydropyrazolo[3,4-b]pyridine-2-carboxylic acid (S)-indan-1-ylamide In analogy to example 2, 50 mg (0.146 mmol) of 6-chloro-4-methyl-3-oxo-1,3-dihydropyrazolo[3,4-b]pyridine-2-carboxylic acid (S)-indan-1-ylamide were reacted with 31 mg (0.22 mmol) of iodomethane in DMF with 2,3,4,6,7,8,9,10-octahydro-pyrimido[1,2-a]azepin (DBU). Yield: 6 mg (12%), M+H+: 357.09.

Example 14

6-Chloro-1,4-dimethyl-3-oxo-1,3-dihydropyrazolo[3,4-b]pyridine-2-carboxylic acid (R)-indan-1-ylamide In analogy to example 2, 103 mg (0.3 mmol) of 6-chloro-4-methyl-3-oxo-1,3-dihydro-pyrazolo[3,4-b]pyridine-2-carboxylic acid (R)-indan-1-ylamide were reacted with 64 mg (0.45 mmol) of iodomethane in DMF with triethylamine. Yield: 56 mg (52%), M+H+: 357.09.

Example 15

1-Benzyl-6-chloro-4-methyl-3-oxo-1,3-dihydropyrazolo[3,4-b]pyridine-2-carboxylic acid hexylamide In analogy to example 2, 50 mg (0.16 mmol) of 6-chloro-4-methyl-3-oxo-1,3-dihydro-pyrazolo[3,4-b]pyridine-2-carboxylic acid hexylamide were reacted with 33 mg (0.19 mmol) of bromomethylbenzene in DMF with triethylamine. Yield: 20 mg (31%), M+H+: 401.16.

Example 16

3-Oxo-6-trifluoromethyl-3H-isoxazolo[5,4-b]pyridine-2-carboxylic acid hexylamide In analogy to example 1c, 47 mg (0.23 mmol) of 6-trifluoromethylisoxazolo-[5,4-b]pyridin-3-ol were reacted with 34.9 mg (0.27 mmol) of 1-isocyanatohexan in THF. Yield: 15 mg (20%), M+H+: 332.2.

Example 17

6-Methyl-3-oxo-3H-isoxazolo[5,4-b]pyridine-2-carboxylic acid hexylamide

In analogy to example 1c, 50 mg (0.33 mmol) of 6-methylisoxazolo[5,4-b]pyridin-3-ol were reacted with 50.8 mg (0.4 mmol) of 1-isocyanatohexane in THF. Yield: 30 mg (32%), M+H+: 278.1.

The following examples were prepared analogously

| Example | Compound | M + H+ |
|---|---|---|
| 18 | 6-Chloro-4-methyl-3-oxo-1,3-dihydro-pyrazolo[3,4-b]pyridine-2-carboxylic acid-(S)-(1,2,3,4-tetrahydro-naphthalen-1-yl)-amide | 357.21 |
| 19 | 6-Hydroxy-4-methyl-3-oxo-1,3-dihydro-pyrazolo[3,4-b]pyridine-2-carboxylic acid-(R)-indan-1-ylamide | 325.14 |

-continued

| Example | Compound | M + H+ |
|---|---|---|
| 20 | 3-Oxo-1,3-dihydro-pyrazolo[3,4-b]pyridine-2-carboxylic acid-2-ethyl-benzylamide | 297.15 |
| 21 | 6-Chloro-4-methyl-3-oxo-1,3-dihydro-pyrazolo[3,4-b]pyridine-2-carboxylic acid-2-ethyl-benzylamide | 345.12 |
| 22 | 4,6-Dimethyl-3-oxo-1,3-dihydro-pyrazolo[3,4-b]pyridine2-carboxylic acid-(R)-indan-1-ylamide | 323.18 |
| 23 | 1-Benzyl-6-chloro-4-methyl-3-oxo-1,3-dihydro-pyrazolo[3,4-b]pyridine-2-carboxylic acid-R)-indan-1-ylamide | 433.23 |
| 24 | 1-Methyl-3-oxo-1,3-dihydro-pyrazolo[3,4-b]pyridine-2-carboxylic acid-(R)-indan-1-ylamide | 309.11 |
| 25 | 6-Chloro-4-methyl-3-oxo-1,3-dihydro-pyrazolo[3,4-b]pyridine-2-carboxylic acid-(R)-(1,2,3,4-etrahydro-naphthalene-1-yl)-amide | 357.08 |
| 26 | 3-Oxo-1,3-dihydro-pyrazolo[3,4-b]pyridine-2-carboxylic acid-(R)-indan-1-ylamide | 295.11 |
| 27 | 6-Chloro-1-cyanomethyl-4-methyl-3-oxo-1,3-dihydro-pyrazolo[3,4-b]pyridine-2-carboxylic acid-(R)-indan-1-ylamide | 382.17 |

We claim:

1. A compound of formula I

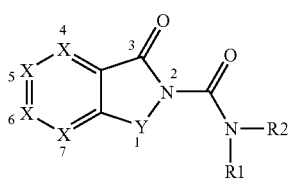

wherein:
X is identically or differently =C(—R)— or =N—, wherein one X is =N—;
Y is NR6 or O;
R is identically or differently hydrogen, halogen, $(C_1-C_6)$-alkyl, $(C_1-C_3)$-haloalkyl, $(C_1-C_3)$-alkyloxy-$(C_1-C_3)$-alkylene, aryl, heterocycle, hydroxy, $(C_1-C_6)$-alkyloxy, $(C_1-C_3)$-haloalkyloxy, aryloxy, cyano, nitro, —S(O)$_p$—$(C_1-C_6)$-alkyl, wherein p=0, 1 or 2, aminosulfonyl, pentafluorosulfanyl, amino, $(C_1-C_6)$-alkylamino, di-$(C_2-C_{12})$-alkylamino, —CO—$(C_1-C_6)$-alkyl, —COOR3, —CO—NR4R5, —O—CO—NR4R5, —O—CO—$(C_1-C_6)$-alkylene-CO—O—$(C_1-C_6)$-alkyl, —O—CO—$(C_1-C_6)$-alkylene-CO—OH or —O—CO—$(C_1-C_6)$-alkylene-CO—NR4R5;
R1 is $(C_8-C_{14})$-bicycle, where the bicycle moiety is optionally substituted one or more times by halogen, $(C_1-C_6)$-alkyl, $(C_1-C_3)$-alkyloxy, hydroxy, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, nitro, trifluoromethyl, trifluoromethyloxy, pentafluorosulfanyl, $(C_1-C_6)$-alkylsulfonyl, or aminosulfonyl;
R2 is hydrogen;
R3 is hydrogen, $(C_1-C_6)$-alkyl, or benzyl;
R4 and R5 are identically or differently hydrogen, $(C_1-C_6)$-alkyl, aryl, $(C_3-C_{12})$-cycloalkyl, $(C_1-C_4)$-alkylene-aryl, or $(C_1-C_4)$-alkylene-$(C_3-C_{12})$-cycloalkyl; and
R6 is hydrogen, $(C_1-C_{10})$-alkyl, $(C_1-C_4)$-alkylene-CN, $(C_1-C_4)$-alkylene-aryl, $(C_1-C_4)$-alkylene-heterocycle, $(C_1-C_4)$-alkylene-$(C_3-C_{12})$-cycloalkyl, or $(C_8-C_{14})$-bicycle, wherein the aryl, heterocycle, cycloalkyl or bicycle moiety is optionally substituted one or more times by halogen, $(C_1-C_6)$-alkyl, $(C_1-C_6)$-alkyloxy, hydroxy, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, nitro $(C_1-C_6)$-alkylsulfonyl, or aminosulfonyl;
or a tautomeric form thereof, or a physiologically tolerated salt thereof.

2. The compound according to claim 1, wherein:
X is identically or differently =C(—R)— or =N—, wherein one X is =N—;
R is identically or differently hydrogen, halogen, $(C_1-C_6)$-alkyl, hydroxy, phenoxy, trifluoromethyl, COOR3, pentafluorosulfanyl, amino, $(C_1-C_6)$-alkylamino, di-$(C_2-C_8)$-alkylamino, $(C_1-C_6)$-alkylsulfonyl, aminosulfonyl, phenyl, $(C_5-C_7)$-heterocycle, $(C_1-C_6)$-alkylcarbonyl, CO—NR4R5, O—CO—NR4R5, O—O—CO—$(C_1-C_6)$-alkylene-CO—O—$(C_1-C_6)$-alkyl, —CO—$(C_1-C_6)$-alkylene-CO—NR4R5 or unsubstituted or mono- or poly-F-substituted $(C_1-C_3)$-alkyloxy;
R1 is $(C_8-C_{14})$-bicycle, where the bicycle moiety is optionally substituted one or more times by halogen, $(C_1-C_6)$-alkyl, $(C_1-C_3)$-alkyloxy, hydroxy, amino, $(C_1-C_6)$-alkylamino, $(C_1-C_6)$-alkoxycarbonyl, $(C_1-C_6)$-alkylcarbonyl, cyano, trifluoromethyl, or trifluoromethyloxy;
R4 and R5 are identically or differently hydrogen, $(C_1-C_6)$-alkyl, $(C_3-C_{12})$-cycloalkyl, phenyl, $(C_1-C_4)$-alkylene-phenyl, or $(C_1-C_4)$-alkylene-$(C_4-C_{12})$-cycloalkyl; and
R6 is hydrogen, $(C_1-C_{10})$-alkyl, $(C_1-C_4)$-alkylene-CN, $(C_1-C_4)$-alkylene-phenyl,$(C_1-C_4)$-alkylene-heterocycle, $(C_1-C_4)$-alkylene-$(C_3-C_{12})$-cycloalkyl, where phenyl, heterocycle, cycloalkyl may be substituted one or more times by preferably halogen, $(C_1-C_6)$-alkyl, $(C_1-C_3)$-alkyloxy, hydroxy, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl;
or a tautomeric form thereof, or a physiologically tolerated salt thereof.

3. The compound according to claim 1, wherein:
X is identically or differently =C(—R)— or =N—, where one X is =N—;
R is identically or differently hydrogen, halogen, $(C_1-C_6)$-alkyl, trifluoromethyl, hydroxy, amino, $(C_1-C_6)$-alkylcarbonyl, COOR3, $(C_1-C_6)$-alkylsulfonyl, pentafluorosulfanyl, or unsubstituted or mono- or poly-F-substituted $(C_1-C_3)$-alkyloxy;
R1 is bicycle of formula Ic

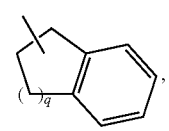

wherein q is 1 or 2, and the bicycle of formula Ic moiety is optionally substituted once to twice by halogen, $(C_1-C_6)$-alkyl, $(C_1-C_6)$-alkyloxy, hydroxy, amino, $(C_1-C_6)$-alkoxycarbonyl, $(C_1-C_6)$-alkylcarbonyl, cyano, trifluoromethyl, or trifluoromethyloxy;
R3 is hydrogen, or $(C_1-C_6)$-alkyl; and R6 is hydrogen, $(C_1$-$C_8)$-alkyl, $(C_1$-$C_2)$-alkylene-CN, $(C_1$-$C_4)$-alkylene-phenyl, or $(C_1$-$C_4)$-alkylene-$(C_4$-$C_{12})$-heteroaryl, wherein the phenyl or heteroaryl moiety is optionally substituted one or more times by halogen, $(C_1$-$C_6)$-alkyl, $(C_1$-$C_3)$-alkyloxy, hydroxy, $(C_1$-$C_6)$-alkoxycarbonyl, $(C_1$-$C_6)$-alkylcarbonyl, or trifluoromethyl;

or a tautomeric form thereof, or a physiologically tolerated salt thereof.

4. The compound according to claim 1, wherein:

X is identically or differently =C(—R)— or =N—, wherein one X is =N—;

R is identically or differently hydrogen, halogen, hydroxy, $(C_1$-$C_6)$-alkyloxy, trifluoromethyl $(C_1$-$C_6)$-alkylcarbonyl or $(C_1$-$C_6)$-alkyl;

R1 is bicycle of formula Ic

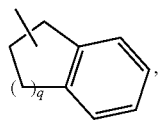

Ic wherein q is 1 or 2, and the bicycle of formula Ic moiety is optionally substituted one to twice by halogen, $(C_1$-$C_6)$-alkyl, $(C_1$-$C_3)$-alkyloxy, $(C_1$-$C_6)$-alkylcarbonyl, or trifluoromethyl; and R6 is hydrogen, $(C_1$-$C_6)$-alkyl, $(C_1$-$C_2)$-alkylene-CN, or $(C_1$-$C_2)$-alkylene-phenyl, wherein the phenyl moiety is optionally substituted one or more times by halogen, $(C_1$-$C_6)$-alkyl, $(C_1$-$C_3)$-alkyloxy, hydroxy, $(C_1$-$C_6)$-alkylcarbonyl, or trifluoromethyl;

or a tautomeric form thereof, or a physiologically tolerated salt thereof.

5. The compound according to claim 1, wherein:

X is identically or differently =C(—R)— or =N—, wherein one X is =N—;

R is identically or differently hydrogen, F, Cl, hydroxy, $(C_1$-$C_6)$-alkyloxy, trifluoromethyl $(C_1$-$C_6)$-alkylcarbonyl or $(C_1$-$C_6)$-alkyl;

R1 is bicycle of formula Ic

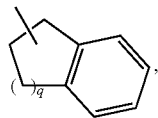

Ic wherein q is 1 or 2, and the bicycle of formula Ic moiety is optionally substituted one to twice by F, Cl, $(C_1$-$C_6)$-alkyl, $(C_1$-$C_3)$-alkyloxy, $(C_1$-$C_6)$-alkylcarbonyl, or trifluoromethyl; and R6 hydrogen, $(C_1$-$C_6)$-alkyl, $(C_1$-$C_2)$-alkylene-CN, $(C_1$-$C_2)$-alkylene-phenyl, where phenyl may be substituted one or more times by $(C_1$-$C_6)$-alkyl, $(C_1$-$C_3)$-alkyloxy, hydroxy, $(C_1$-$C_6)$-alkylcarbonyl, trifluoromethyl;

or a tautomeric form thereof, or a physiologically tolerated salt thereof.

6. The compound according to claim 1 wherein

X is identically or differently =C(—R)— or =N—, wherein one X is =N—;

R is identically or differently hydrogen, Cl, hydroxy, methyl, or trifluoromethyl;

R1 is bicycle of formula Id

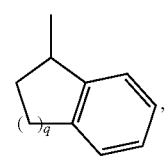

Id wherein q is 1 or 2, and

R6 is hydrogen, $CH_2$—CN, methyl, butyl, or benzyl;

or a tautomeric form thereof, or a physiologically tolerated salt thereof.

7. The compound according to claim 1, wherein:

X in position 5 and 6 is identically or differently =C(—R)—, and in one of positions 4 and 7 is =N—, and in the other position is =C(—R)—;

or a tautomeric form thereof, or a physiologically tolerated salt thereof.

8. The compound according to claim 1, wherein:

X in position 4, 5 and 6 is identically or differently =C(—R)—, and in position 7 is =N—, or a tautomeric form thereof, or a physiologically tolerated salt thereof.

9. A pharmaceutical composition comprising the compound according to claim 1, or a tautomeric form thereof, or a physiologically tolerated salt thereof, and a pharmaceutically acceptable carrier.

10. The pharmaceutical composition according to claim 9, further comprising at least one additional active ingredient selected from the group consisting of antidiabetics, hypoglycemic active ingredients, HMGCoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP citrate lyase inhibitors, squalene synthetase inhibitors, lipoprotein antagonists, lipase inhibitors, insulins, sulfonylureas, biguanides, meglitinides, thiazolidinediones, α-glucosidase inhibitors, active ingredients acting on the ATP-dependent potassium channel of the beta cells, CART agonists, NPY agonists, MC4 agonists, orexin antagonists, H3 agonists, TNF agonists, CRF antagonists, CRF BP antagonists, urocortin agonists, β3 agonists, melanocyte-stimulating hormone agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists, bromocriptine, Doprexin, lipase inhibitors, amylase inhibitors, PPAR modulators, RXR modulators, TR-βagonists and amphetamines.

11. A process for preparing a pharmaceutical composition comprising at least one compound according to claim 1, or a tautomeric form thereof, or a physiologically tolerated salt thereof, which comprises mixing the compound according to claim 1, or the tautomeric form thereof, or the physiologically tolerated salt thereof, with a pharmaceutically suitable carrier and converting this mixture into a form suitable for administration.

12. A process for preparing the compound according to claim 1, comprising reacting an azolopyridin-3-ol derivative of formula II with an isocyanate of formula III;

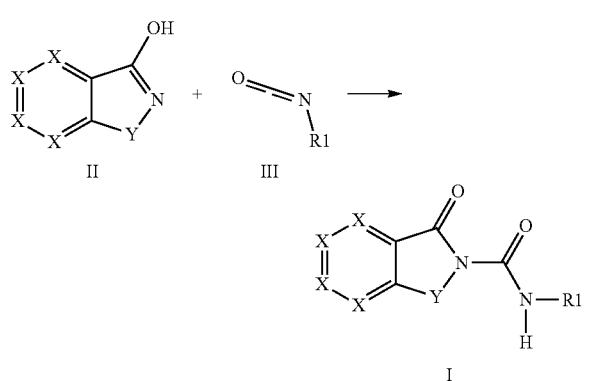

or
acylating an azolopyridin-3-ol derivative of formula II with a carbamoyl chloride of formula VI;

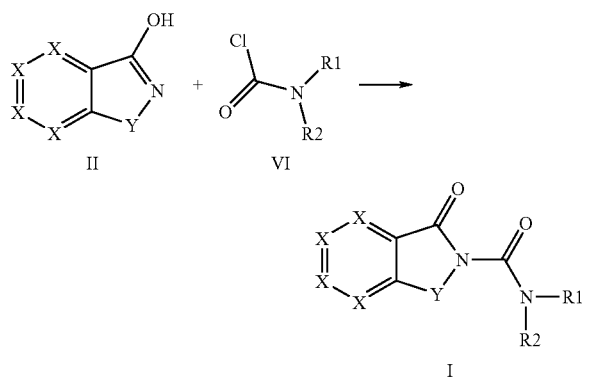

or
reacting an azolopyridin-3-ol derivative of formula II first with phosgene or an equivalent, and then with an amine of formula VII, wherein X, Y, R1 and R2 are as defined in claim 1,

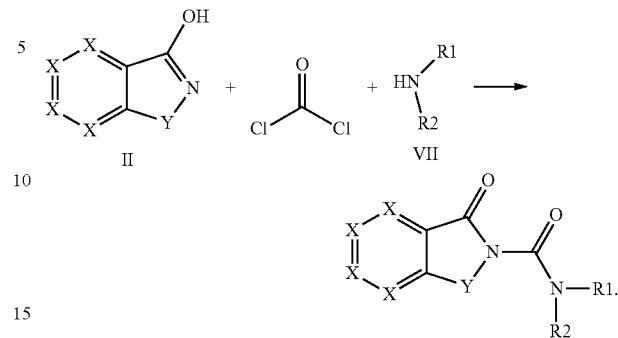

13. The process according to claim 12, wherein the equivalent of phosgene is trichloromethyl chlorocarbonate, ditrichloromethyl carbonate or 4-nitrophenyl chloroformate.

14. A process for preparing the compound according to claim 1, wherein Y is NR6, comprising reacting a compound of formula IVa with a compound of formula V, wherein L is halogen, a methanesulfonyl group or a tosyl group, and R1, X, Y and R6 are as defined in claim 1

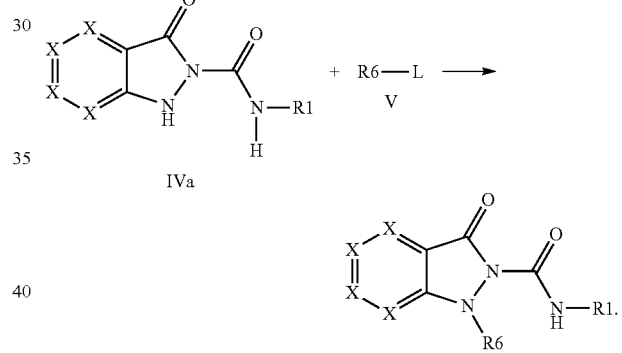

* * * * *